US008889848B2

(12) United States Patent
Delaney, IV et al.

(10) Patent No.: US 8,889,848 B2
(45) Date of Patent: Nov. 18, 2014

(54) HCV GENOTYPE 3 REPLICONS

(75) Inventors: William E. Delaney, IV, Foster City, CA (US); Guofeng Cheng, Foster City, CA (US); Hongmei Mo, Palo Alto, CA (US); Simin Xu, Palo Alto, CA (US); Mei Yu, San Francisco, CA (US); Amoreena Corsa, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 33 days.

(21) Appl. No.: 13/542,551

(22) Filed: Jul. 5, 2012

(65) Prior Publication Data

US 2013/0052633 A1 Feb. 28, 2013

Related U.S. Application Data

(60) Provisional application No. 61/509,989, filed on Jul. 20, 2011, provisional application No. 61/504,853, filed on Jul. 6, 2011.

(51) Int. Cl.

| | |
|---|---|
| ***C12Q 1/70*** | (2006.01) |
| ***C12Q 1/66*** | (2006.01) |
| ***C12N 15/86*** | (2006.01) |
| ***C12N 5/10*** | (2006.01) |
| ***C12N 5/071*** | (2010.01) |
| ***C07K 14/005*** | (2006.01) |
| *C12Q 1/68* | (2006.01) |
| *C12N 15/64* | (2006.01) |
| *C12N 15/65* | (2006.01) |

(52) U.S. Cl.

CPC ..... *C07K 14/005* (2013.01); *C12N 2770/24222* (2013.01); *C12N 2770/24231* (2013.01); *C12N 2770/24243* (2013.01); *G01N 2333/9513* (2013.01); *G01N 2333/186* (2013.01); *C12Q 1/707* (2013.01); *G01N 2500/00* (2013.01); *C12N 15/86* (2013.01)

USPC .......... 536/23.72; 435/5; 435/320.1; 435/370

(58) Field of Classification Search

CPC ........ C12N 15/64; C12N 15/65; C12N 15/86; C12N 2015/79; C12N 2770/24222; C12N 2770/24231; C12N 2770/24243; C12Q 1/70; C12Q 1/707

See application file for complete search history.

(56) References Cited

FOREIGN PATENT DOCUMENTS

| | | |
|---|---|---|
| WO | WO-2004/039970 | 5/2004 |
| WO | WO-2005/053516 | 6/2005 |
| WO | WO-2009/071488 | 6/2009 |
| WO | WO-2011/038737 | 4/2011 |

OTHER PUBLICATIONS

Gottwein et al. Robust hepatitis C genotype 3a cell culture releasing adapted intergenotypic 3a/2a (S52/JFH1) viruses. Gastroenterology 2007, vol. 133, p. 1614-1626.*

Peng et al. Development of robust hepatitis C virus genotype 4 subgenomic replicons. Gastroenterology 2013, vol. 144, p. 59-61.*

Gottwein et al. Novel infectious cDNA clones of hepatitis C virus genotype 3a (Strain S52) and 4a (Strain ED43): genetic analyses and in vivo pathogenesis studies. Journal of Virology 2010, vol. 84, No. 10, p. 5277-5293.*

U.S. Appl. No. 13/542,554, filed Jul. 5, 2012, Delaney, IV.

Author unknown, "Hepatitis C virus partial NS3 protease", retrieved from EBI <http://www.ebi.ac.uk/ena/data/view/ABD65842&display=text>, database accession No. ABD65842 sequence, 2006.

Blight et al., "HCV Replicon Systems", Source Hepatitis C Viruses: Genomes and Molecular Biology, 2006, pp. 311-351.

International Search Report and Written Opinion for PCT/US2012/045592 dated Nov. 15, 2012.

International Search Report and Written Opinion for PCT/US2012/045593 dated Dec. 3, 2012.

Khaliq et al., "Down-regulation of IRES containing 5'UTR of HCV genotype 3a using siRNAs", Virology Journal, vol. 8, No. 1, 2011, pp. 223-224.

O'Boyle et al., "Development of a Cell-based High-throughput Specificity Screen Using a Hepatitis C Virus-Bovine Viral Diarrhea Virus Dual Replicon Assay", Antimicrobial Agents and Chemotherapy, vol. 49, No. 4, 2005, pp. 1346-1353.

Peng et al., "825 Development and Molecular Characterization of a Robust Genotype 4 Hepatitis C Virus Subgenomic Replicon", Journal of Hepatology, vol. 56, 2012, 1 page.

Winters et al., "Hepatitis C virus protease gene diversity in patients coinfected with human immunodeficiency virus", Journal of Virology, vol, 80, No. 8, 2006, pp. 4196-4199.

Zekri et al., "Consensus siRNA for Inhibition of HCV genotype-4 replication", Virology Journal, London, vol. 6, No. 1, 2009, 9 pgs.

Kamal et al. Hepatitis C Genotype 4: What we know and what we don't yet know. Hepatology 2008, vol. 47, pp. 1371-1383.

Kuiken et al. Nomenclature and numbering of the hepatitis C virus, Methods Mol Biol. 2009;510:33-53.

Scheel et al. Development of JFH1-based cell culture systems for hepatitis C virus genotype 4a and evidence for cross-genotype neutralization. Proceedings from the National Academy of Sciences of the USA 2008, vol. 105, No. 3, p. 997-1002.

* cited by examiner

*Primary Examiner* — Louise Humphrey

(74) *Attorney, Agent, or Firm* — Sheppard Mullin Richter & Hampton LLP

(57) ABSTRACT

Replicons of genotype 3 of hepatitis C virus (HCV) are provided. These replicons contains adaptive mutations giving rise to the HCV's capability to replicate in vitro. Methods of preparing genotype 3 replicons and methods of using these replicons to screen antiviral agents are also provided.

24 Claims, 7 Drawing Sheets

(A)

(B)

SEQUENCE LISTING

```
<160> NUMBER OF SEQ ID NOS: 13

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ggcgcgcca                                                               9


<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

ggccggccgc ggccgcaa                                                    18


<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

acgcgtatg                                                               9


<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

atagcgctat ggcttccaag gtgtacga                                         28


<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

aatgcggccg ctcagaagaa ctcgtca                                          27


<210> SEQ ID NO 6
<211> LENGTH: 10
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 6
ggcgcgccca 10

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7 ggccggcca 9

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
aacaccatcg gcgcgcccat ggcttccaag gtgtacgac 39

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
tcggggccat acgcgtatcg tgtttttcaa agg 33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
aacaccatcg gcgcgccaaa ccaagttcaa tag 33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
tcggggccat acgcgtatcg tgtttttcaa agg 33

<210> SEQ ID NO 12
<211> LENGTH: 9555
<212> TYPE: DNA
<213> ORGANISM: Hepatitis C virus

<400> SEQUENCE: 12

```
acctgcctct tacgaggcga cactccacca tggatcactc ccctgtgagg aacttctgtc      60
ttcacgcgga aagcgcctag ccatggcgtt agtacgagtg tcgtgcagcc tccaggaccc     120
cccctcccgg gagagccata gtggtctgcg gaaccggtga gtacaccgga atcgctgggg     180
tgaccgggtc ctttcttgga gcaacccgct caatacccag aaatttgggc gtgcccccgc     240
gagatcacta gccgagtagt gttgggtcgc gaaaggcctt gtggtactgc ctgatagggt     300
gcttgcgagt gccccgggag gtctcgtaga ccgtgcaaca tgagcacact tcctaaacct     360
caaagaaaaa ccaaaagaaa caccatccgt cgcccacagg acgttaagtt cccgggtggc     420
ggacagatcg ttggtggagt atacgtgttg ccgcgcaggg gcccacgatt gggtgtgcgc     480
gcgacgcgta aaacttctga acggtcacag cctcgcggac gacgacagcc tatccccaag     540
gcgcgtcgga gcgaaggccg gtcctgggct cagcccgggt acccttggcc cctctatggt     600
aatgagggct gcgggtgggc agggtggctc ctgtccccac gcggctcccg tccatcttgg     660
ggcccaaacg acccccggcg gaggtcccgc aatttgggta aagtcatcga taccettacg     720
tgcggattcg ccgacctcat ggggtacatc ccgctcgtcg gcgctcccgt aggaggcgtc     780
gcaagagccc tcgcgcatgg cgtgagggcc cttgaagacg ggataaattt tgcaacaggg     840
aacttgcccg gttgctcctt ttctatcttc cttcttgctc tgttctcctg cttagttcat     900
cctgcagcta gtctagagtg gcggaatacg tctggcctct atgtccttac caacgactgt     960
tccaatagca gtattgtgta tgaggccgat gacgtcattc tgcacacacc cggctgtgta    1020
ccttgtgttc aggacggcaa tacatccacg tgctggaccc cagtgacacc tacggtggca    1080
gtcaggtacg tcggagcaac caccgcttcg atacgcagtc atgtggacct attagtgggc    1140
gcggccacgc tgtgctctgc gctctatgtg ggtgatatgt gtggggccgt ctttctcgtg    1200
ggacaagcct tcacgttcag acctcgtcgc catcaaacgg tccagacctg taactgctcg    1260
ctgtacccag gccatgtttc aggacatcga atggcttggg atatgatgat gaattggtcc    1320
cccgctgtgg gtatggtggt ggcgcacatc ctgcgattgc cccagacctt gtttgacata    1380
ctggccgggg cccattgggg catcttggcg ggcctagcct attattctat gcagggcaac    1440
tgggccaagg tcgctattgt catgattatg ttttcagggg tcgatgccga aacatatgtc    1500
accggtggca gtgtagctca tagtgccaga gggttaacta gcctttttag tatgggcgcc    1560
aagcagaaac tgcagttggt caacaccaat ggctcgtggc acatcaacag tactgccctg    1620
aactgcaatg agtccataaa caccgggttc atagctgggt tgttttatta ccataagttc    1680
aactctactg gatgtcctca aaggctcagc agctgcaagc ccatcatttc cttcaggcag    1740
gggtggggcc ccttgacaga tgctaacatc accggtcctt ctgatgatag accgtattgc    1800
tggcactacg cacctagacc ttgtagtgtt gtcccggcat caagtgtctg cggccctgtg    1860
tactgcttca caccatcgcc agtggtcgta ggcactactg atatcaaagg caggccgacc    1920
tacaactggg gtgagaatga gacagatgtg ttcctgctgg agtccctgcg gcctcccagt    1980
ggccggtggt ttggatgcgc gtggatgaac tccacggggt tcctcaagac gtgtggagct    2040
ccccccttgta acatctatgg gggtgagggg gatcccgaaa atgagacaga cctcttctgc    2100
cccaccgact gcttcaggaa acatcctgag gccacataca gccggtgtgg tgcggggccc    2160
tggttgacac ctcgctgcat ggtcgactat ccataccggc tttggcatta cccatgtaca    2220
gtcaatttca cattgttcaa ggtgaggatg tttgtgggcg gatttgaaca ccggtttacc    2280
```

-continued

```
gccgcttgta actggaccag gggggagcgc tgcaatatcg aggatcgtga tcgcagcgag   2340
caacatccgc tgctgcattc aacaactgag cttgctatac tgccttgctc tttcacgccc   2400
atgcctgcat tgtcaacagg tctaatacac ctccaccaaa atatcgtgga tgtccaatac   2460
ctttatggtg ttggatctga catggtggga tgggcgctga aatgggagtt cgtcatcctc   2520
gttttcctcc tcctggcaga cgcacgcgtg tgcgttgccc tttggctgat gctgatggta   2580
tcacaagcag aagcagcctt ggagaacctt gtcacgctga acgccgtcgc tgctgctggg   2640
acacatggta ttggctggta cctggtagcc ttttgcgcgg cgtggtacgt gcggggtaaa   2700
cttgtcccgc tgacgatcta cggcctgacg ggtctttggt ccctagcatt gcttgtcctc   2760
ttgctccccc aacgggcgta tgcttggtcg ggtgaagaca gcgccactct cggcgctggg   2820
gtcttggccc tcttcggctt ctttacctta tcaccctggt acaagcattg gatcggccgc   2880
ctcatgtggt ggaaccagta cactatatgt agatgcgagg ccgcccttca agtgtgggtc   2940
ccccccttac ttgcacgcgg gagtagggac ggtgtcatcc tgctaacaag cttgctttat   3000
ccatccttaa tttttgacat cactaagctg ctgatagcag taataggccc attatactta   3060
atacaggccg ccatcactac cacccccctac tttgtgcgcg cacatgtact ggtccgcctt   3120
tgcatgctcg tgcgctccgt gatgggggga aagtacttcc agatggccat actgagcatt   3180
ggcagatggt tcaacaccta cctatatgac cacctagcgc caatgcaaca ttgggccgca   3240
gctggcctca aagacctagc agtggccact gaacctgtaa tatttagtcc catggaaatt   3300
aaggtcatca cctggggcgc ggacacagcg gcttgcggag atattctttg cgggctgccg   3360
gtctccgcgc gattaggccg tgaggtattg ttgggacctg ctgatgatta tcgggaaatg   3420
ggttggcgtc tgttggcccc gatcacagca tacgcccagc aaactagggg ccttcttggg   3480
actattgtga ccagcttgac tggcagggat aagaacattg tgaccggtga agtgcaggtg   3540
ctttctacgg ctacccagac cttcctaggt acaacagtag ggggggttat gtggactgtt   3600
taccatggtg caggttcgaa aacgctcgcg ggcgccaaac atcccgcgct ccaaatgtac   3660
acaaatgtgg atcaggacct cgttgggtgg ccagcccctc caggggctaa gtctcttgaa   3720
ccgtgcgcct gcgggtctgc agacttatac ttggttaccc gcgatgccga tgtcatccct   3780
gctcggcgca ggggggactc cacagcgagc ttgctcagtc ctagacctct cgcctgtctc   3840
aaaggttcct ctggaggtcc tgttatgtgc ccttctgggc atgttgcggg gatctttagg   3900
gctgctgtgt gcaccagagg tgtagcaaaa gccctacagt tcgtaccagt ggaaaccctt   3960
agcacacagg ctaggtctcc atctttctct gacaattcaa ctcctcctgc tgttccacag   4020
agctatcaag tagggtacct tcatgccccg accggcagcg gtaagagcac aaaggtcccg   4080
gccgcttatg tagcacaagg atataatgtt ctcgtgctga atccatcggt ggcggccaca   4140
ctaggcttcg gctctttcat gtcgcgtgcc tatgggatcg accccaacat ccgcactggg   4200
aaccgcaccg tcacaactgg tgctaaacta acctattcca cctacggtaa gtttcttgcg   4260
gacgggggtt gctccggggg ggcatatgat gtgatcatct gtgatgaatg tcatgcccaa   4320
gacgctacta gcatattggg tataggcacg gtcttagatc aggctgagac ggccggggtg   4380
aggttgacgg ttttagcaac agcaactccc ccaggcagca tcactgtgcc acattctaac   4440
atcgaagaag tggccctggg ctctgaaggt gagatccctt tctacggtaa ggctataccg   4500
atagccctgc tcaagggggg gaggcacctt atcttttgcc attccaagaa aaaatgtgat   4560
gaggtggcag ccaaactcag aggcatgggg ctcaacgctg tggcgtacta taggggtctc   4620
gatgtgtccg tcataccaac aacaggagac gtcgtagttt gcgctactga cgccctcatg   4680
```

-continued actggattca ccggagactt cgattctgtc atagattgca acgtggctgt tgaacagtac 4740
gttgacttca gcctggaccc caccttttcc attgagaccc gcaccgctcc ccaagatgcg 4800
gtttcccgca gccaacgtcg tggccgtacg ggccgaggta gactcggtac gtaccgatat 4860
gttgccccgg gtgaaagacc gtctggaatg tttgactcgg ttgttctctg tgagtgctat 4920
gacgcgggct gctcgtggta cgatctgcag ccagctgaga ccacagtcag actgagagct 4980
tacttgaaca cgccggggtt acctgtctgc caggaccatt tagacttttg ggagagcgtc 5040
ttcactggat tgactcacat agacgcccac tttctgtcac agactaagca acagggactt 5100
aacttctcgt tcctaactgc ctaccaagcc actgtgtgtg cccgcgcaca ggcttctcca 5160
ccaagttggg acgagacgtg gaagtgtctc gtgcggctta agccaacact acatggacct 5220 acgcccttc tatatcggtt agggcctgtc caaaatgaca tctgcttgac acaccccgtc 5280
acaaaataca tcatggcatg catgtcagct gatctggaag taaccaccag cacctgggtg 5340
ttgcttggag ggtcctygc ggccctagcg gcctactgct tgtcagtcgg ctgcgttgtg 5400
atcgtgggtc atattgagct gagaggcaag ccggcactcg taccggacag agaggtgttg 5460
tatcaacaat acgatgagat ggaggagtgc tcacaagccg ccccatatat cgaacaagct 5520
caggcaatcg cccaccagtt caaggaaaaa atcctaggac tgctgcagcg agccacccag 5580
caacaagctg tcatcgagcc catagtagct accaactggc aaaaacttga gaccttctgg 5640
cacaagcata tgtggaattt tgtgagtggg atccaatacc tagcaggcct ctccactttg 5700
cccggcaacc cagctgtggc gtctcttatg gcgttcactg cttcagtcac cagtcccctg 5760
acgaccaacc agactatgtt ttttaacata ctcgggggt gggtcgccac ccatttggca 5820
gggccccaga gctcttccgc gttcgtggta agcggcttag ccggcgctgc catagggggt 5880
ataggcctgg gcagggtctt gctggacatc ctggcaggat acggagctgg tgtctcaggc 5940
gccttggtgg cttttaagat catgggagga gaactcccca ctactgagga catggtcaac 6000
ctgttgcccg ccatactatc tccgggcgct ctcgtcgtcg gtgtgatatg cgctgccata 6060
ctacgtcgac acgtaggacc tggggaggga gcggtacagt ggatgaacag gctcatcgca 6120
ttcgcgtccc ggggcaacca cgtctcacca acgcactatg ttcccgagag cgatgctgca 6180
gcgagggtca ccgcattgct gagttctcta actgtcacaa gtctgctccg gcggttacac 6240
aagtggatca atgaagacta cccaagccct tgcagcggcg attggctgcg tgacatctgg 6300
gactgggttt gctcggtgtt gtccgacttc aagacgtggc tctctgctaa gattatgcca 6360
gcactccctg ggctgccctt catctcctgt caaaagggat acaagggcgt gtggcggggg 6420
gatggtgtga tgtcgacacg ctgtccttgc ggggcatcaa tcactggcca cgtgaagaat 6480
gggtccatgc ggcttgcggg gccgcgtatg tgtgctaaca tgtggcacgg tactttcccc 6540
atcaatgagt acaccaccgg acccagcaca ccttgcccat cacccaacta cactcgcgca 6600
ctatggcgcg tggctgccag cagctacgtt gaggtgcgcc gggtggggga cttccattat 6660
attacggggg ctacagaaga tgagctcaag tgtccgtgcc aagtgccggc tgctgagttc 6720
tttactgaag tggatggggt gagactccac cgttacgccc ctccatgtaa gcccctgttg 6780
agagaagaga tcactttctc ggtagggttg cattcctacg cgataggatc tcaactcccc 6840
tgtgagccag aaccagatgt ttctgtgttg acctcgatgt tgagagaccc ttctcatatc 6900
accgccgaga cggcagcgcg ccgccttgcg cgcgggtccc ctccatcaga ggcaagctca 6960
tccgccagcc aactatcggc tccgtcgttg aaggccactt gccagacgca taggcctcat 7020

-continued

```
ccagacgctg agctggtgga cgccaacttg ttatggcggc aagagatggg cagcaacatt   7080
acacgggtgg agtctgaaac gaaggttgtg attcttgatt cattcgaacc tctgagagcc   7140
gaagctgacg acgccgagct ctcggtggct gcagagtgtt tcaagaagcc tcccaagtat   7200
cctccagccc ttcctatctg ggccaggccg gactacaacc ctccactgtt ggaccgctgg   7260
aaagcaccgg attatgtacc accaactgtc catggatgtg ccttaccacc acggggcgct   7320
ccaccggtgc ctcctcctcg gaggaaaaga acaatccagc tggacggctc caatgtgtcc   7380
gcggcgctag ctgcgctagc ggaaaaatca ttcccgaccc caaaatcgca ggaagagaat   7440
agctcatcct ctggggtcga cacacagtcc agcactacct ccaggatgcc cccctctcca   7500
ggaggggagt ccgactcaga gtcatgctcg tccatgcctc ctctcgaggg agagccgggc   7560
gatccggact tgagttgcga ctcttggtcc accgttagtg acaacgagga gcagagcgtg   7620
gtctgctgct ctatgtcgta ctcttggacc ggtgccctga taacaccatg tagtgctgag   7680
gaggagaaac tgcccatcag cccactcagc aattctttgt tgagacatca taacctagtc   7740
tattcaacgt cgtctagaag cgcttctcag cgtcagagga aggttacctt cgacagactg   7800
caggtgctcg acgaccatta taagactgca ttaaaggagg tgaaggagcg agcgtctagg   7860
gtgaaggccc gcatgctcac catcgaggaa gcgtgcgcgc tcgtccctcc tcactctgcc   7920
cggtcgaagt tcgggtatag tgcgaaggac gttcgctcct tgtccagcag ggccattgac   7980
cagatccgct ccgtctggga ggacctgctg gaagacacca caactccaat tccaaccacc   8040
atcatggcga agaacgaggt gttttgtgtg gacccccgcta aaggggggccg caagcccgct   8100
cgcctcattg tgtaccctga tctgggggtg cgtgtctgtg agaaacgcgc cctatatgac   8160
gtgatacaga agttgtcaat tgagacgatg ggttccgctt atggattcca atactcgcct   8220
caacagcggg tcgaacgtct actgaagatg tggacctcaa agaaaacccc cttggggttc   8280
tcatatgaca cccgctgctt tgactcaact gtcactgaac aggacatcag ggtagaagag   8340
gagatatatc aatgctgtaa ccttgaaccg gaggccagga aagtgatctc ctccctcacg   8400
gagcggcttt actgcggggg ccctatgttc aacagcaagg gggcccagtg tggttatcgc   8460
cgttgccgtg ccagtggagt tctgcctacc agctttggca atacaatcac ttgttacatc   8520
aaggccacag cggccgcgaa ggccgcaggc ctccggaacc cggactttct tgtctgcgga   8580
gatgatttgg tcgtggtggc tgagagtgat ggcgtcgatg aggatagagc agccctgaga   8640
gccttcacgg aggctatgac caggtactct gctccacccg gagatgcccc acagcccacc   8700
tatgaccttg agctcattac atcttgctcc tctaacgtct ccgtggcacg ggacgacaag   8760
gggaggaggt attattacct cacccgtgat gccactactc ccctagcccg cgcggcttgg   8820
gaaacagccc gtcacactcc agtcaactcc tggttaggta acatcatcat gtacgcgcct   8880
accatctggg tgcgcatggt aatgatgaca cactttttct ccatactcca atcccaggag   8940
atacttgatc gaccccttga ctttgaaatg tacggggcca cttactctgt cactccgctg   9000
gatttaccag caatcattga aagactccat ggtctaagcg cattcacgct ccacagttac   9060
tctccagtag agctcaatag ggtcgcgggg acactcagga agcttgggtg ccccccccta   9120
cgagcttgga gacatcgggc acgagcagtg cgcgccaagc ttatcgccca gggagggaag   9180
gccaaaatat gcggccttta tctcttcaat tgggcggtac gcaccaagac caatctcact   9240
ccactgccag ccactggcca gttggatttg tccagctggt ttacggttgg tgtcggcggg   9300
aacgacattt atcacagcgt gtcacgtgcc cgaacccgcc atttgctgct ttgcctactc   9360
ctactaacgg taggggtagg catctttctc ctgccagctc ggtgagctgg taggataaca   9420
```

```
ctccattctt ttttttttt ttttttttt ttttttttt ttttttttt ttttttttt   9480

ttttttttt tttttctttt ccttttccct tcttttctga cctttaatct tccttcttag   9540

gtggctccat cttag                                                 9555


<210> SEQ ID NO 13
<211> LENGTH: 3021
<212> TYPE: PRT
<213> ORGANISM: Hepatitis C virus

<400> SEQUENCE: 13

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
```

-continued

```
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
    370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Arg Pro Thr Tyr
        515                 520                 525

Asn Trp Gly Glu Asn Glu Thr Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Ala Gly Thr
        755                 760                 765
```

-continued

```
His Gly Ile Gly Trp Tyr Leu Val Ala Phe Cys Ala Ala Trp Tyr Val
    770                 775                 780

Arg Gly Lys Leu Val Pro Leu Thr Ile Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
    850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
            900                 905                 910

Thr Thr Thr Pro Tyr Phe Val Arg Ala His Val Leu Val Arg Leu Cys
        915                 920                 925

Met Leu Val Arg Ser Val Met Gly Gly Lys Tyr Phe Gln Met Ala Ile
    930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly  Asp Ile Leu Cys Gly  Leu Pro Val
        995                 1000                1005

Ser Ala  Arg Leu Gly Arg Glu  Val Leu Leu Gly Pro  Ala Asp Asp
    1010                1015                1020

Tyr Arg  Glu Met Gly Trp Arg  Leu Leu Ala Pro Ile  Thr Ala Tyr
    1025                1030                1035

Ala Gln  Gln Thr Arg Gly Leu  Leu Gly Thr Ile Val  Thr Ser Leu
    1040                1045                1050

Thr Gly  Arg Asp Lys Asn Ile  Val Thr Gly Glu Val  Gln Val Leu
    1055                1060                1065

Ser Thr  Ala Thr Gln Thr Phe  Leu Gly Thr Thr Val  Gly Gly Val
    1070                1075                1080

Met Trp  Thr Val Tyr His Gly  Ala Gly Ser Lys Thr  Leu Ala Gly
    1085                1090                1095

Ala Lys  His Pro Ala Leu Gln  Met Tyr Thr Asn Val  Asp Gln Asp
    1100                1105                1110

Leu Val  Gly Trp Pro Ala Pro  Pro Gly Ala Lys Ser  Leu Glu Pro
    1115                1120                1125

Cys Ala  Cys Gly Ser Ala Asp  Leu Tyr Leu Val Thr  Arg Asp Ala
    1130                1135                1140

Asp Val  Ile Pro Ala Arg Arg  Arg Gly Asp Ser Thr  Ala Ser Leu
    1145                1150                1155

Leu Ser  Pro Arg Pro Leu Ala  Cys Leu Lys Gly Ser  Ser Gly Gly
    1160                1165                1170
```

-continued

Pro Val Met Cys Pro Ser Gly His Val Ala Gly Ile Phe Arg Ala
1175 1180 1185

Ala Val Cys Thr Arg Gly Val Ala Lys Ala Leu Gln Phe Val Pro
1190 1195 1200

Val Glu Thr Leu Ser Thr Gln Ala Arg Ser Pro Ser Phe Ser Asp
1205 1210 1215

Asn Ser Thr Pro Pro Ala Val Pro Gln Ser Tyr Gln Val Gly Tyr
1220 1225 1230

Leu His Ala Pro Thr Gly Ser Gly Lys Ser Thr Lys Val Pro Ala
1235 1240 1245

Ala Tyr Val Ala Gln Gly Tyr Asn Val Leu Val Leu Asn Pro Ser
1250 1255 1260

Val Ala Ala Thr Leu Gly Phe Gly Ser Phe Met Ser Arg Ala Tyr
1265 1270 1275

Gly Ile Asp Pro Asn Ile Arg Thr Gly Asn Arg Thr Val Thr Thr
1280 1285 1290

Gly Ala Lys Leu Thr Tyr Ser Thr Tyr Gly Lys Phe Leu Ala Asp
1295 1300 1305

Gly Gly Cys Ser Gly Gly Ala Tyr Asp Val Ile Ile Cys Asp Glu
1310 1315 1320

Cys His Ala Gln Asp Ala Thr Ser Ile Leu Gly Ile Gly Thr Val
1325 1330 1335

Leu Asp Gln Ala Glu Thr Ala Gly Val Arg Leu Thr Val Leu Ala
1340 1345 1350

Thr Ala Thr Pro Pro Gly Ser Ile Thr Val Pro His Ser Asn Ile
1355 1360 1365

Glu Glu Val Ala Leu Gly Ser Glu Gly Glu Ile Pro Phe Tyr Gly
1370 1375 1380

Lys Ala Ile Pro Ile Ala Leu Leu Lys Gly Gly Arg His Leu Ile
1385 1390 1395

Phe Cys His Ser Lys Lys Lys Cys Asp Glu Val Ala Ala Lys Leu
1400 1405 1410

Arg Gly Met Gly Leu Asn Ala Val Ala Tyr Tyr Arg Gly Leu Asp
1415 1420 1425

Val Ser Val Ile Pro Thr Thr Gly Asp Val Val Val Cys Ala Thr
1430 1435 1440

Asp Ala Leu Met Thr Gly Phe Thr Gly Asp Phe Asp Ser Val Ile
1445 1450 1455

Asp Cys Asn Val Ala Val Glu Gln Tyr Val Asp Phe Ser Leu Asp
1460 1465 1470

Pro Thr Phe Ser Ile Glu Thr Arg Thr Ala Pro Gln Asp Ala Val
1475 1480 1485

Ser Arg Ser Gln Arg Arg Gly Arg Thr Gly Arg Gly Arg Leu Gly
1490 1495 1500

Thr Tyr Arg Tyr Val Ala Pro Gly Glu Arg Pro Ser Gly Met Phe
1505 1510 1515

Asp Ser Val Val Leu Cys Glu Cys Tyr Asp Ala Gly Cys Ser Trp
1520 1525 1530

Tyr Asp Leu Gln Pro Ala Glu Thr Thr Val Arg Leu Arg Ala Tyr
1535 1540 1545

Leu Asn Thr Pro Gly Leu Pro Val Cys Gln Asp His Leu Asp Phe
1550 1555 1560

Trp Glu Ser Val Phe Thr Gly Leu Thr His Ile Asp Ala His Phe

-continued

```
    1565                1570                1575

Leu Ser  Gln Thr Lys Gln Gln  Gly Leu Asn Phe Ser  Phe Leu Thr
    1580                1585                1590

Ala Tyr  Gln Ala Thr Val Cys  Ala Arg Ala Gln Ala  Ser Pro Pro
    1595                1600                1605

Ser Trp  Asp Glu Thr Trp Lys  Cys Leu Val Arg Leu  Lys Pro Thr
    1610                1615                1620

Leu His  Gly Pro Thr Pro Leu  Leu Tyr Arg Leu Gly  Pro Val Gln
    1625                1630                1635

Asn Asp  Ile Cys Leu Thr His  Pro Val Thr Lys Tyr  Ile Met Ala
    1640                1645                1650

Cys Met  Ser Ala Asp Leu Glu  Val Thr Thr Ser Thr  Trp Val Leu
    1655                1660                1665

Leu Gly  Gly Val Leu Ala Ala  Leu Ala Ala Tyr Cys  Leu Ser Val
    1670                1675                1680

Gly Cys  Val Val Ile Val Gly  His Ile Glu Leu Arg  Gly Lys Pro
    1685                1690                1695

Ala Leu  Val Pro Asp Arg Glu  Val Leu Tyr Gln Gln  Tyr Asp Glu
    1700                1705                1710

Met Glu  Glu Cys Ser Gln Ala  Ala Pro Tyr Ile Glu  Gln Ala Gln
    1715                1720                1725

Ala Ile  Ala His Gln Phe Lys  Glu Lys Ile Leu Gly  Leu Leu Gln
    1730                1735                1740

Arg Ala  Thr Gln Gln Gln Ala  Val Ile Glu Pro Ile  Val Ala Thr
    1745                1750                1755

Asn Trp  Gln Lys Leu Glu Thr  Phe Trp His Lys His  Met Trp Asn
    1760                1765                1770

Phe Val  Ser Gly Ile Gln Tyr  Leu Ala Gly Leu Ser  Thr Leu Pro
    1775                1780                1785

Gly Asn  Pro Ala Val Ala Ser  Leu Met Ala Phe Thr  Ala Ser Val
    1790                1795                1800

Thr Ser  Pro Leu Thr Thr Asn  Gln Thr Met Phe Phe  Asn Ile Leu
    1805                1810                1815

Gly Gly  Trp Val Ala Thr His  Leu Ala Gly Pro Gln  Ser Ser Ser
    1820                1825                1830

Ala Phe  Val Val Ser Gly Leu  Ala Gly Ala Ala Ile  Gly Gly Ile
    1835                1840                1845

Gly Leu  Gly Arg Val Leu Leu  Asp Ile Leu Ala Gly  Tyr Gly Ala
    1850                1855                1860

Gly Val  Ser Gly Ala Leu Val  Ala Phe Lys Ile Met  Gly Gly Glu
    1865                1870                1875

Leu Pro  Thr Thr Glu Asp Met  Val Asn Leu Leu Pro  Ala Ile Leu
    1880                1885                1890

Ser Pro  Gly Ala Leu Val Val  Gly Val Ile Cys Ala  Ala Ile Leu
    1895                1900                1905

Arg Arg  His Val Gly Pro Gly  Glu Gly Ala Val Gln  Trp Met Asn
    1910                1915                1920

Arg Leu  Ile Ala Phe Ala Ser  Arg Gly Asn His Val  Ser Pro Thr
    1925                1930                1935

His Tyr  Val Pro Glu Ser Asp  Ala Ala Ala Arg Val  Thr Ala Leu
    1940                1945                1950

Leu Ser  Ser Leu Thr Val Thr  Ser Leu Leu Arg Arg  Leu His Lys
    1955                1960                1965
```

-continued

```
Trp Ile  Asn Glu Asp Tyr Pro  Ser Pro Cys Ser Gly  Asp Trp Leu
    1970                 1975                 1980

Arg Asp  Ile Trp Asp Trp Val  Cys Ser Val Leu Ser  Asp Phe Lys
    1985                 1990                 1995

Thr Trp  Leu Ser Ala Lys Ile  Met Pro Ala Leu Pro  Gly Leu Pro
    2000                 2005                 2010

Phe Ile  Ser Cys Gln Lys Gly  Tyr Lys Gly Val Trp  Arg Gly Asp
    2015                 2020                 2025

Gly Val  Met Ser Thr Arg Cys  Pro Cys Gly Ala Ser  Ile Thr Gly
    2030                 2035                 2040

His Val  Lys Asn Gly Ser Met  Arg Leu Ala Gly Pro  Arg Met Cys
    2045                 2050                 2055

Ala Asn  Met Trp His Gly Thr  Phe Pro Ile Asn Glu  Tyr Thr Thr
    2060                 2065                 2070

Gly Pro  Ser Thr Pro Cys Pro  Ser Pro Asn Tyr Thr  Arg Ala Leu
    2075                 2080                 2085

Trp Arg  Val Ala Ala Ser Ser  Tyr Val Glu Val Arg  Arg Val Gly
    2090                 2095                 2100

Asp Phe  His Tyr Ile Thr Gly  Ala Thr Glu Asp Glu  Leu Lys Cys
    2105                 2110                 2115

Pro Cys  Gln Val Pro Ala Ala  Glu Phe Phe Thr Glu  Val Asp Gly
    2120                 2125                 2130

Val Arg  Leu His Arg Tyr Ala  Pro Pro Cys Lys Pro  Leu Leu Arg
    2135                 2140                 2145

Glu Glu  Ile Thr Phe Ser Val  Gly Leu His Ser Tyr  Ala Ile Gly
    2150                 2155                 2160

Ser Gln  Leu Pro Cys Glu Pro  Glu Pro Asp Val Ser  Val Leu Thr
    2165                 2170                 2175

Ser Met  Leu Arg Asp Pro Ser  His Ile Thr Ala Glu  Thr Ala Ala
    2180                 2185                 2190

Arg Arg  Leu Ala Arg Gly Ser  Pro Pro Ser Glu Ala  Ser Ser Ser
    2195                 2200                 2205

Ala Ser  Gln Leu Ser Ala Pro  Ser Leu Lys Ala Thr  Cys Gln Thr
    2210                 2215                 2220

His Arg  Pro His Pro Asp Ala  Glu Leu Val Asp Ala  Asn Leu Leu
    2225                 2230                 2235

Trp Arg  Gln Glu Met Gly Ser  Asn Ile Thr Arg Val  Glu Ser Glu
    2240                 2245                 2250

Thr Lys  Val Val Ile Leu Asp  Ser Phe Glu Pro Leu  Arg Ala Glu
    2255                 2260                 2265

Ala Asp  Asp Ala Glu Leu Ser  Val Ala Ala Glu Cys  Phe Lys Lys
    2270                 2275                 2280

Pro Pro  Lys Tyr Pro Pro Ala  Leu Pro Ile Trp Ala  Arg Pro Asp
    2285                 2290                 2295

Tyr Asn  Pro Pro Leu Leu Asp  Arg Trp Lys Ala Pro  Asp Tyr Val
    2300                 2305                 2310

Pro Pro  Thr Val His Gly Cys  Ala Leu Pro Pro Arg  Gly Ala Pro
    2315                 2320                 2325

Pro Val  Pro Pro Pro Arg Arg  Lys Arg Thr Ile Gln  Leu Asp Gly
    2330                 2335                 2340

Ser Asn  Val Ser Ala Ala Leu  Ala Ala Leu Ala Glu  Lys Ser Phe
    2345                 2350                 2355
```

-continued

```
Pro Thr  Pro Lys Ser Gln Glu  Glu Asn Ser Ser Ser  Ser Gly Val
    2360                 2365                 2370

Asp Thr  Gln Ser Ser Thr Thr  Ser Arg Met Pro Pro  Ser Pro Gly
    2375                 2380                 2385

Gly Glu  Ser Asp Ser Glu Ser  Cys Ser Ser Met Pro  Pro Leu Glu
    2390                 2395                 2400

Gly Glu  Pro Gly Asp Pro Asp  Leu Ser Cys Asp Ser  Trp Ser Thr
    2405                 2410                 2415

Val Ser  Asp Asn Glu Glu Gln  Ser Val Val Cys Cys  Ser Met Ser
    2420                 2425                 2430

Tyr Ser  Trp Thr Gly Ala Leu  Ile Thr Pro Cys Ser  Ala Glu Glu
    2435                 2440                 2445

Glu Lys  Leu Pro Ile Ser Pro  Leu Ser Asn Ser Leu  Leu Arg His
    2450                 2455                 2460

His Asn  Leu Val Tyr Ser Thr  Ser Ser Arg Ser Ala  Ser Gln Arg
    2465                 2470                 2475

Gln Arg  Lys Val Thr Phe Asp  Arg Leu Gln Val Leu  Asp Asp His
    2480                 2485                 2490

Tyr Lys  Thr Ala Leu Lys Glu  Val Lys Glu Arg Ala  Ser Arg Val
    2495                 2500                 2505

Lys Ala  Arg Met Leu Thr Ile  Glu Glu Ala Cys Ala  Leu Val Pro
    2510                 2515                 2520

Pro His  Ser Ala Arg Ser Lys  Phe Gly Tyr Ser Ala  Lys Asp Val
    2525                 2530                 2535

Arg Ser  Leu Ser Ser Arg Ala  Ile Asp Gln Ile Arg  Ser Val Trp
    2540                 2545                 2550

Glu Asp  Leu Leu Glu Asp Thr  Thr Thr Pro Ile Pro  Thr Thr Ile
    2555                 2560                 2565

Met Ala  Lys Asn Glu Val Phe  Cys Val Asp Pro Ala  Lys Gly Gly
    2570                 2575                 2580

Arg Lys  Pro Ala Arg Leu Ile  Val Tyr Pro Asp Leu  Gly Val Arg
    2585                 2590                 2595

Val Cys  Glu Lys Arg Ala Leu  Tyr Asp Val Ile Gln  Lys Leu Ser
    2600                 2605                 2610

Ile Glu  Thr Met Gly Ser Ala  Tyr Gly Phe Gln Tyr  Ser Pro Gln
    2615                 2620                 2625

Gln Arg  Val Glu Arg Leu Leu  Lys Met Trp Thr Ser  Lys Lys Thr
    2630                 2635                 2640

Pro Leu  Gly Phe Ser Tyr Asp  Thr Arg Cys Phe Asp  Ser Thr Val
    2645                 2650                 2655

Thr Glu  Gln Asp Ile Arg Val  Glu Glu Glu Ile Tyr  Gln Cys Cys
    2660                 2665                 2670

Asn Leu  Glu Pro Glu Ala Arg  Lys Val Ile Ser Ser  Leu Thr Glu
    2675                 2680                 2685

Arg Leu  Tyr Cys Gly Gly Pro  Met Phe Asn Ser Lys  Gly Ala Gln
    2690                 2695                 2700

Cys Gly  Tyr Arg Arg Cys Arg  Ala Ser Gly Val Leu  Pro Thr Ser
    2705                 2710                 2715

Phe Gly  Asn Thr Ile Thr Cys  Tyr Ile Lys Ala Thr  Ala Ala Ala
    2720                 2725                 2730

Lys Ala  Ala Gly Leu Arg Asn  Pro Asp Phe Leu Val  Cys Gly Asp
    2735                 2740                 2745

Asp Leu  Val Val Val Ala Glu  Ser Asp Gly Val Asp  Glu Asp Arg
```

-continued

```
    2750                2755                2760

Ala Ala  Leu Arg Ala Phe Thr  Glu Ala Met Thr Arg  Tyr Ser Ala
    2765                2770                2775

Pro Pro  Gly Asp Ala Pro Gln  Pro Thr Tyr Asp Leu  Glu Leu Ile
    2780                2785                2790

Thr Ser  Cys Ser Ser Asn Val  Ser Val Ala Arg Asp  Asp Lys Gly
    2795                2800                2805

Arg Arg  Tyr Tyr Tyr Leu Thr  Arg Asp Ala Thr Thr  Pro Leu Ala
    2810                2815                2820

Arg Ala  Ala Trp Glu Thr Ala  Arg His Thr Pro Val  Asn Ser Trp
    2825                2830                2835

Leu Gly  Asn Ile Ile Met Tyr  Ala Pro Thr Ile Trp  Val Arg Met
    2840                2845                2850

Val Met  Met Thr His Phe Phe  Ser Ile Leu Gln Ser  Gln Glu Ile
    2855                2860                2865

Leu Asp  Arg Pro Leu Asp Phe  Glu Met Tyr Gly Ala  Thr Tyr Ser
    2870                2875                2880

Val Thr  Pro Leu Asp Leu Pro  Ala Ile Ile Glu Arg  Leu His Gly
    2885                2890                2895

Leu Ser  Ala Phe Thr Leu His  Ser Tyr Ser Pro Val  Glu Leu Asn
    2900                2905                2910

Arg Val  Ala Gly Thr Leu Arg  Lys Leu Gly Cys Pro  Pro Leu Arg
    2915                2920                2925

Ala Trp  Arg His Arg Ala Arg  Ala Val Arg Ala Lys  Leu Ile Ala
    2930                2935                2940

Gln Gly  Gly Lys Ala Lys Ile  Cys Gly Leu Tyr Leu  Phe Asn Trp
    2945                2950                2955

Ala Val  Arg Thr Lys Thr Asn  Leu Thr Pro Leu Pro  Ala Thr Gly
    2960                2965                2970

Gln Leu  Asp Leu Ser Ser Trp  Phe Thr Val Gly Val  Gly Gly Asn
    2975                2980                2985

Asp Ile  Tyr His Ser Val Ser  Arg Ala Arg Thr Arg  His Leu Leu
    2990                2995                3000

Leu Cys  Leu Leu Leu Leu Thr  Val Gly Val Gly Ile  Phe Leu Leu
    3005                3010                3015

Pro Ala  Arg
    3020
```

HCV GENOTYPE 3 REPLICONS

CROSS-REFERENCE TO RELATED APPLICATIONS

This application claims the benefit under 35 U.S.C. §119 (e) of U.S. Provisional Application Ser. No, 61/504,853 filed Jul. 6, 2011 and Ser. No. 61/509,989 filed Jul. 20, 2011, the content of each of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on May 30, 2014, is named 37JD192880US_SL.txt and is 42,092 bytes in size.

FIELD OF THE DISCLOSURE

The disclosure is directed to hepatitis C replicons of genotype 3 and methods of preparing and using the replicons.

STATE OF THE ART

Chronic hepatitis C virus (HCV) infection remains a significant global heath burden with an estimated 160 million people infected world wide. The current standard of care is 24 to 48 week courses of pegylated interferon plus ribavirin. Due to the partial efficacy and poor tolerability of this regimen, the discovery and development of new antiviral agents has been intensely pursued. Recently, these efforts have culminated in the FDA approval of two NS3 protease inhibitors (boceprevir and telaprevir) for use in combination with pegylated interferon and ribavirin for the treatment of chronic genotype 1 HCV infection. Many other inhibitors are in advanced clinical development, however, the majority are being developed to treat genotype 1 infections.

HCV is a positive-strand RNA virus that exhibits extraordinary genetic diversity. Six major genotypes (i.e. genotype 1-6) along with multiple subtypes (e.g. genotype 1a, 1b, 1c etc.) have been reported. Genotypes 1, 2 and 3 have worldwide distributions. Genotypes 1a or 1b are generally predominant in North America, South America, Europe and Asia. However, genotypes 2 and 3 are common and can constitute 20 to 50% of infections in many of these areas. Genotype 4a is the predominant in the Middle East and many African countries; up to 15% of the population of Egypt is infected with HCV and 93% of infections are genotype 4. Genotype 5 is prevalent in South Africa, while Genotype 6 is most common in Asia. Although most continents and countries have a "dominant" genotype, infected populations are almost universally made up of a mixture of multiple genotypes. Furthermore, the geographical distribution and diversity (epidemiology) of HCV infection is continuously evolving, due to large-scale immigration and widespread intravenous drug use. For instance, genotype 4a has noticeably spread into central and northern Europe. This presents a clinical challenge, since it is well documented that individual genotypes respond differently to both direct antivirals and immunomodulatory therapies, including the current standard of care.

HCV replicons are self-replicating RNA sequences derived from the HCV genome and have served as workhorses both for molecular virology studies and drug discovery. To date, replicons have been established from two genotypes and three subtypes (genotypes 1a, 1b and 2a). These replicons have been crucial in multiple aspects of drug discovery and development including the identification of novel inhibitor classes, the optimization of clinical candidates and the characterization of clinical resistance. Recently, there has been increasing interest in developing next-generation drugs that are active against all major HCV genotypes. Ideally, the approval of "pan-genotypic" drugs and regimens will greatly simplify the treatment of HCV.

A key step in the pursuit of pan-genotypic treatment regimens will be the development of in vitro tools that allow the study of all major genotypes and subtypes. Replicons derived from sequences of additional major genotypes (i.e. those other than genotype 1a, 1b or 2a), however, have not been generated. In particular, despite the worldwide prevalence of genotype 3 HCV in the Middle East, North Africa and Europe, no genotype 3 replicons have been described.

SUMMARY

It has been discovered, unexpectedly, that clonal cell lines stably replicating genotype 3 replicons were obtained by transcribing and electroporating subgenomic genotype 3 cDNAs into HCV permissive cell lines. Adaptive mutations have been identified from these clones, as compared to the wildtype virus. When these mutations were engineered by site-directed mutagenesis and introduced into the cell lines, HCV genotype 3 replications ensued. One such adaptive mutation is N607S at NS3 and another such adaptive mutation is P89L at NS3. The establishment of a robust genotype 3 replicon system provides powerful tools to facilitate drug discovery and development efforts.

Accordingly, one embodiment of the present disclosure provides a genotype 3 hepatitis C viral (HCV) RNA construct that is capable of replication in a eukaryotic cell, wherein the RNA sequence comprises a 5'NTR, an internal ribosome entry site (IRES), sequences encoding one or more of NS3, NS4A, NS4B, NS5A or NS5B, and a 3'NTR.

In one aspect, the construct comprises an adaptive mutation in NS3, NS4A, NS4B, NS5A or NS5B. In another aspect, the mutation comprises an isoleucine at residue 232 in NS5A. In yet another aspect, the mutation comprises, in NS3, a serine at residue 607.

In yet another aspect, the mutation comprises, in NS3, a leucine at residue 89. In some aspects, the mutation further comprises one or more of an arginine at residue 41, a threonine at residue 166, a threonine at residue 379, a glycine at residue 534, a glutamic acid at residue 583, and/or a cysteine at residue 1. In yet another aspect, the mutation further comprises one of more provided in Tables 7-9.

Moreover, DNA that transcribes to the RNA construct, viral particles that include the RNA construct, and cells containing such DNA or RNA are also provided.

Also provided, in another embodiment, is an NS3 protein of HCV genotype 3 that comprises a serine at residue 607 and/or a leucine at residue 89. In another embodiment, provided is an NS5A protein that comprises an isoleucine at residue 232. Polynucleotides encoding these proteins and antibodies that specifically recognize the proteins are also provided.

In another embodiment, the present disclosure provides an isolated cell comprising a genotype 3 hepatitis C viral (HCV) RNA that replicates in the cell. In one aspect, there is an absence, in the cell, of a DNA construct encoding the RNA. In another aspect, the cell comprises at least 10 copies, or alternatively at least about 100, 500, 1000, 2000, 5000, 10,000, $1\times10^5$, $1\times10^6$, $1\times10^7$, $1\times10^8$ or $1\times10^9$ copies of the RNA. In any of such aspects, the RNA can be a subgenomic HCV sequence or a full-length HCV sequence and can include one or more of the adaptive mutations described above.

Methods of improving the capability of a genotype 3 HCV viral RNA to replicate in a eukaryotic cell are also provided, comprising substituting residue 607 of NS3 with a serine and/or substituting residue 89 of NS3 with a leucine. Further mutations can include one of more of an arginine at residue 41, a threonine at residue 166, a threonine at residue 379, a glycine at residue 534, a glutamic acid at residue 583, and/or a cysteine at residue 1 or those provided in Tables 7-9.

Still provided, in one embodiment, is a method of identifying an agent that inhibits the replication or activity of a genotype 3 HCV, comprising contacting a cell of any of the above embodiments with a candidate agent, wherein a decrease of replication or a decrease of the activity of a protein encoded by the RNA indicates that the agent inhibits the replication or activity of the HCV. Alternatively, the method comprises contacting the lysate of a cell of any of the above embodiments with a candidate agent, wherein a decrease of the activity of a protein encoded by the RNA indicates that the agent inhibits the activity of the HCV.

BRIEF DESCRIPTION OF THE DRAWINGS

The disclosure is best understood from the following detailed description when read in conjunction with the accompanying drawings. Included in the drawings are the following figures.

DETAILED DESCRIPTION

Figure 1:
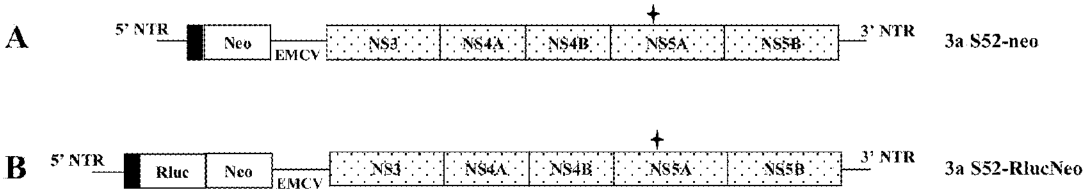
FIG. 1 is a schematic diagram of genotype 3a replicon constructs. An S52 3a strain (Accession #: GU814264) replicon encodes a neomycin (A) or a Renilla luciferase (Rluc)-neomycin fusion reporter (B). The synthesized replicon incorporated the following elements from 5' to 3': the S52 5'UTR; the neomycin phosphotransferase II gene (neo) or Rluc-Neo gene; the encephalomyocarditis virus (EMCY) IRES; the NS3-NS5B polyprotein region of S52 including an NS5A adaptive mutation (S22040 and the 3'UTR of S52. Solid boxes indicate HCV core sequence. Dot shaded boxes indicate the HCV polyprotein sequence. "+" indicates the S2204I adaptive mutation. The 5' and 3' non-translated regions (NTR), and EMCV IRES are indicated.

Prior to describing this disclosure in greater detail, the following terms will first be defined.

It is to be understood that this disclosure is not limited to particular embodiments described, as such may, of course, vary. It is also to be understood that the terminology used herein is for the purpose of describing particular embodiment's only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a thread" includes a plurality of threads.

Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

| 1-Letter | 3-Letter | Amino Acid |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention. In one embodiment, the homologous peptide is one that shares the same functional characteristics as those described, including one or more of the adaptive mutations.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant. GenBank+EMBL+DDBJ+PDB+GenBank CDS translations+SwissProtein+SPupdate+PIR. Details of these programs can be found at the following Internet address: www.ncbi.nlm.nih.gov/blast/Blast.cgi, last accessed on Jul. 15, 2011.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells, or alternatively from a prokaryotic cells as described above. Non-limiting examples include simian, bovine, porcine, murine, rats, avian, reptilian and human.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The antibodies can be polyclonal or monoclonal and can be isolated from any suitable biological source, e.g., murine, rat, sheep and canine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "isolated" as used herein refers to molecules or biological or cellular materials being substantially free from other materials or when referring to proteins or polynucleotides, infers the breaking of covalent bonds to remove the protein or polynucleotide from its native environment. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. The term "isolated" is also used herein to refer to cells or tissues that are isolated from other cells or tissues and is meant to encompass both cultured and engineered cells or tissues.

Hepatitis C virus or "HCV" is a small (55-65 nm in size), enveloped, positive-sense single-stranded RNA virus of the family Flaviviridae. Hepatitis C virus is the cause of hepatitis C in humans. The hepatitis C virus particle consists of a core of genetic material (RNA), surrounded by an icosahedral protective shell of protein, and further encased in a lipid (fatty) envelope of cellular origin. Two viral envelope glycoproteins, E1 and E2, are embedded in the lipid envelope.

Hepatitis C virus has a positive sense single-stranded RNA genome. The genome consists of a single open reading frame that is 9600 nucleotide bases long. This single open reading frame is translated to produce a single protein product, which is then further processed to produce smaller active proteins.

At the 5' and 3' ends of the RNA are the UTR, that are not translated into proteins but are important to translation and replication of the viral RNA. The 5' UTR has a ribosome binding site (IRES—Internal ribosome entry site) that starts the translation of a very long protein containing about 3,000 amino acids. This large pre-protein is later cut by cellular and viral proteases into the 10 smaller proteins that allow viral replication within the host cell, or assemble into the mature viral particles.

Structural proteins made by the hepatitis C virus include Core protein, E1 and E2; nonstructural proteins include NS2, NS3, NS4, NS4A, NS4B, NS5, NS5A, and NS5B.

Based on genetic differences between HCV isolates, the hepatitis C virus species is classified into six genotypes (1-6) with several subtypes within each genotype (represented by letters). Subtypes are further broken down into quasispecies based on their genetic diversity. The preponderance and distribution of HCV genotypes varies globally. For example, in North America, genotype 1a predominates followed by 1b, 2a, 2b, and 3a. In Europe, genotype 1b is predominant followed by 2a, 2b, 2c, and 3a. Genotypes 4 and 5 are found almost exclusively in Africa. Genotype is clinically important in determining potential response to interferon-based therapy and the required duration of such therapy. Genotypes 1 and 4 are less responsive to interferon-based treatment than are the other genotypes (2, 3, 5 and 6). Duration of standard interferon-based therapy for genotypes 1 and 4 is 48 weeks, whereas treatment for genotypes 2 and 3 is completed in 24 weeks.

Sequences from different HCV genotypes can vary as much as 33% over the whole viral genome and the sequence variability is distributed equally throughout the viral genome, apart from the highly conserved 5' UTR and core regions and the hypervariable envelope (E) region.

HCV genotypes can be identified with various methods known in the art. PCR-based genotyping with genotype-specific primers was first introduced in 1992, in particular with primers targeting the core region. Commercial kits (e.g., InnoLipa® by Innogenetics (Zwijindre, Belgium)) are also available. Direct sequencing, in the vein, can be used for more reliable and sensitive genotyping.

Serologic genotyping uses genotype-specific antibodies and identifies genotypes indirectly. Two commercially available serologic genotyping assays have been introduced, including a RIBA SIA assay from Chiron Corp. and the Murex HCV serotyping enzyme immune assay from Nurex Diagnostics Ltd.

Sequences of genotype 3 HCV have been identified. For instance, GenBank accession # GU814264 provides the sequence of a subgenomic genotype 3a replicon based on the S52 infectious clone. Further discussion of the genotype 3 and their sequences are clinical impacts can be found at Zein *Clin. Microbiol. Rev,* 13(2):223-35 (2000).

The term "replicon" refers to a DNA molecule or RNA molecule, or a region of DNA or RNA, that replicates from a single origin of replication. For most prokaryotic chromosomes, the replicon is the entire chromosome. In some aspects, a replicon refers to a DNA or RNA construct that replicates in a cell in vitro. In one aspect, a replicon can replicate to produce at least about 10, or alternatively, at least about 100, 500, 1000, 2000, 5000, 10,000, $1\times10^5$, $1\times10^6$, $1\times10^7$, $1\times10^8$ or $1\times10^9$ copies of the replicon in a cell in vitro. Alternatively, a replicon's replication efficiency can be measured by producing certain amount of viral RNA in total RNA that includes cellular RNA. In one aspect, a replicon can produce at least about 1000, $1\times10^4$, $1\times10^5$, $1\times10^6$, $1\times10^7$, $1\times10^8$, $1\times10^9$, $1\times10^{10}$, $1\times10^{11}$, or $1\times10^{12}$ copies of the replicon per microgram of total RNA or cellular RNA.

A "subgenomic" HCV sequence refers to a HCV sequence that does not include all sequences of a wild-type HCV. In one aspect, a subgenomic HCV or a subgenomic HCV replicon does not include the E1, E2 or C regions. In another aspect, a subgenomic HCV or a subgenomic HCV replicon includes all or part of the 5' UTR, NS3, NS4A, NS4B, NS5A, NS5B and 3' UTR sequences. In contrast, a "full-length" or "full genome" HCV or HCV replicon includes E1, E2 and C regions. In some aspects, both a subgenomic and a full-length HCV replicon can include one or more of a reporter gene (e.g., luciferase), a marker gene (e.g., Neo), and an IRES (e.g., EMCV IRES) sequence.

A virus particle (or virion) consists of the genetic material made from either DNA or RNA of a virus and a protein coat that protects the genetic material. In one aspect, an envelope of lipids surrounds the protein coat when they are outside a cell.

The term "adaptive mutation" of a HCV replicon of a certain genotype refers to a mutation, as compared to a wild-type HCV sequence of the genotype, that enables the wild-type replicon to replicate in a cell, in particular in a eukaryotic cell such as a mammalian cell and in vitro, or enhances a HCV replicon's ability to replicate. It is contemplated that an adaptive mutation can favorably influence assembly of the replicase complex with host cell-specific protein, or alternatively promote interactions of the protein that includes the adaptive mutation (e.g., NS3, NS4A, NS4B, NS5A etc) with cellular proteins involved in host cell antiviral defenses.

A "reporter gene" refers to a gene that can be attached to a regulatory sequence of another gene of interest in cell culture, animals or plants, to facilitate identification of this other gene. Reporter genes are often used as an indication of whether a certain gene has been taken up by or expressed in the cell or organism population. Non-limiting examples of reporter gene include the luciferase gene and the green fluorescent protein gene.

A "marker gene" or "selectable marker" refers to a gene that protects the organism from a selective agent that would normally kill it or prevent its growth. One non-limiting example is the neomycin phosphotransferase gene (Neo), which upon expression confers resistance to G418, an aminoglycoside antibiotic similar in structure to gentamicin B1.

HCV Genotype 3 Replicon Constructs

The present disclosure relates, in general, to the unexpected discovery that clonal cell lines stably replicating genotype 3 replicons can be obtained by transcribing and electroporating subgenomic genotype 3 cDNAs into HCV permissive cell lines. From the clonal cells, adaptive mutations are then identified. One such adaptive mutation is N607S at NS3. Another adaptive mutation is P89L. The S2204I (S232I within NS5A) mutation is also applicable in this genotype. The effect of any one or more of these mutations can be further enhanced by one or more of Q41R (NS3), A166T (NS3), A379T (NS3 helicase domain), S534G (NS3 helicase domain), K583E (NS3 helicase domain), S1C (NS4A) or those provided in Tables 7-9.

Identification of these mutations suggests that these mutations contribute to the HCV's capability to replicate in cells in vitro, a phenomenon not observed with wild-type HCV genotype 3 RNA. Such contribution has been confirmed by engineering the mutations, by site-directed mutagenesis, into genotype 3 RNA and introducing them into the cell lines. Genotype 3 HCV RNA, with such mutations, successfully replicated in the cell lines. Therefore, the Applicant has demonstrated that the Applicant has prepared HCV genotype 3 replicons capable of replication in vitro and has identified adaptive mutations leading to such capabilities.

Accordingly, in one embodiment, the present disclosure provides a genotype 3 hepatitis C viral (HCV) RNA that is capable of replication in a host cell. In one aspect, the replication is in vitro. In one aspect, the replication is productive replication. In another aspect, the cell is a eukaryotic cell such as a mammalian cell or a human cell. In yet another aspect, the cell is a hepatoma cell. In some aspects, the RNA can replicate to produce at least 10 copies of the RNA in a cell. In another aspect, the number of copies is at least about 100, 500, 1000, 2000, 5000, 10,000, $1\times10^5$, $1\times10^6$, $1\times10^7$, $1\times10^8$ or $1\times10^9$.

The HCV RNA can be a subgenomic HCV sequence. It is specifically contemplated that a full-length HCV replicon containing any or more of such adaptive mutations is also capable to replicate. Still further, an entire HCV virus of the corresponding genotype containing the adaptive mutation(s) would be infectious and capable to replicate. In any such case, RNA can include one or more of 5'NTR, an internal ribosome entry site (IRES), sequences encoding NS3, NS4A, NS4B, NS5A and NS5B, and a 3'NTR. In one aspect, the RNA includes, from 5' to 3' on the positive-sense nucleic acid, a functional HCV 5' non-translated region (5'NTR) comprising an extreme 5'-terminal conserved sequence; an HCV polyprotein coding region; and a functional HCV 3' non-translated region (3'NTR) comprising an extreme 3'-terminal conserved sequence.

In any of the above embodiments, the HCV RNA can include an adaptive mutation that enables the RNA to replicate in the cell. Such adaptive mutations can include an isoleucine at residue 232 at NS5A, and/or a serine at residue 607 for NS3. Another adaptive mutation is P89L. The effect of any one or more of these mutations can be further enhanced by one or more of Q41R (NS3), A166T (NS3), A379T (NS3 helicase domain), S534G (NS3 helicase domain, K583 (NS3 helicase domain). S1C (NS4A) or those provided in Tables 7-9.

In one embodiment, provided are replicons listed in Table 3. It is specifically contemplated that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s) and/or activities.

In another embodiment, provided is a genotype 3 HCV RNA construct comprising a 5'NTR, an internal ribosome entry site (IRES), sequences encoding NS3, NS4A, NS4B, NS5A and NS5B, and a 3'NTR, wherein the construct is capable to replicate in a eukaryotic cell. In one aspect, the construct comprises an adaptive mutation in NS3, NS4A, NS4B, NS5A or NS5B. The mutation, in one aspect, comprises an isoleucine at residue 232 in NS5A, and in another aspect, comprises, in NS3, a serine at residue 607 and/or a leucine at residue 89, in some aspects, the genotype 3 is genotype 3a.

In any of the above embodiments, the HCV RNA can further comprise a marker gene for selection. A non-limiting example of such marker gene is a neomycin phosphotransferase gene. Other examples are well known in the art.

In any of the above embodiments, the HCV RNA can further comprise a reporter gene. A non-limiting example of such marker gene is a luciferase gene. Other examples are well known in the art.

The RNA construct of any of the above embodiment can further comprise sequences encoding one or more of C, E1 or E2. In one aspect, the RNA construct is a full-length HCV replicon.

The disclosure also provides a single or double-stranded DNA that can be transcribed to a RNA construct of any of the above embodiment, a viral particle comprising a RNA construct of any of the above embodiment, or an isolated cell comprising a RNA construct of any of the above embodiment.

In one aspect of any such embodiments, the genotype 3 is genotype 3a. In yet another aspect, provided is a polynucleotide encoding the protein of any of such embodiments. The polynucleotide can be RNA or DNA. In another aspect, provided is an RNA or DNA construct comprising the polynucleotide. In yet another aspect, provided is a cell comprising the polynucleotide. Still in one aspect, provided is an antibody that specifically recognizes a protein of any of the above embodiments.

HCV Genotype 3 Replicons and Cells Containing the Replicons

Another embodiment of the present disclosure provides an isolated cell comprising a hepatitis C viral (HCV) RNA that is genotype 3, wherein the HCV RNA replicates in the cell. In one aspect, there is an absence, in the cell, of a DNA construct encoding the RNA and thus copies of the HCV RNA are not transcribed from a DNA, such as cDNA, construct.

In one aspect, the cell comprises at least 10 copies of the RNA. In another aspect, the cell comprises at least 100, 500, 1000, 2000, 5000, 10,000, $1\times10^5$, $1\times10^6$, $1\times10^7$, $1\times10^8$ or $1\times10^9$ copies of the RNA.

The HCV RNA can be subgenomic HCV sequence or a full-length HCV sequence. In either case, RNA can include one or more of 5'NTR, an internal ribosome entry site (IRES), sequences encoding NS3, NS4A, NS4B, NS5A and NS5B, and a 3'NTR.

In any of the above embodiments, the HCV RNA can include an adaptive mutation that enables the RNA to replicate in the cell. Such adaptive mutations can include an isoleucine at residue 232 at NS5A.

In one embodiment, provided are replicons listed in Table 3. It is contemplated are that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s).

In one aspect, the cell is a eukaryotic cell such as a mammalian cell and in particular a human cell. In another aspect, the cell is hepatoma cell, such as but not limited to a Huh7 cell (e.g., Huh7-Lunet, 51C and 1C). In some aspects, the cell is placed at an in vitro or ex vivo condition.

Methods of Preparing Genotype 3 Replicons

After HCV genotype 3 replicons are identified, as shown in Example 1, introduction of the relevant adaptive mutation into a corresponding genotype HCV RNA can result in the RNA's capability to replicate, in particular in a mammalian cell in vitro. Accordingly, the present disclosure provides a method of improving the capability of a genotype 3 HCV viral RNA to replicate in a eukaryotic cell, comprising substituting residue 607 of NS3 with a serine or residue 89 of NS3 with a leucine. In one aspect, an residue 232 mutation or any secondary mutation provided herein can further be introduced into the RNA.

Methods of Screening HCV Inhibitors Targeting Genotype 3

Numerous known and unknown HCV inhibitors have been tested for their efficiency in inhibiting the genotype 3 HCV, in comparison with genotype 1b (Example 1). Some showed higher efficacy for genotype 3, and some were not as efficacious. The usefulness of the new identified genotype 3 replicons, therefore, is adequately demonstrated.

Thus, the present disclosure also provides, in one embodiment, a method of identifying an agent that inhibits the replication or activity of a genotype 3 HCV, comprising contacting a cell of any embodiment of the present disclosure with a candidate agent, wherein a decrease of replication or a decrease of activity of a protein encoded by the RNA indicates that the agent inhibits the replication or activity of the HCV. In some aspects, the protein is a protease, such as any or more of NS3, NS4A, NS4B, NS5A or NS5B. Replication of the RNA, in one aspect, can be measured by a reporter gene on the RNA, such as the luciferase gene.

Provided in another embodiment is a method of identifying an agent that the activity of a genotype 3 HCV, comprising contacting the lysate of a cell of any embodiment of the present disclosure with a candidate agent, wherein a decrease of the activity of a protein encoded by the RNA indicates that the agent inhibits the activity of the HCV. In some aspects, the protein is a protease, such as any or more of NS3, NS4A, NS4B, NS5A or NS5B. In one aspect, the method further comprises measuring the replication of the RNA or the activity of the protein encoded by the RNA.

A HCV inhibitor (or "candidate agent") can be a small molecule drug that is an organic compound, a peptide or a protein such as antibodies, or nucleic acid-based such as siRNA. In May 2011, the Food and Drug Administration approved 2 drugs for Hepatitis C, boceprevir and telaprevir. Both drugs block an enzyme that helps the virus reproduce. Boceprevir is a protease inhibitor that binds to the HCV NS3 active site on hepatitis C genotype 1. Telaprevir inhibits the hepatitis C virus NS3.4A serine protease.

More conventional HCV treatment includes a combination of pegylated interferon-alpha-2a or pegylated interferon-alpha-2b (brand names Pegasys or PEG-Intron) and the antiviral drug ribavirin. Pegylated interferon-alpha-2a plus ribavirin may increase sustained virological response among patients with chronic hepatitis C as compared to pegylated interferon-alpha-2b plus ribavirin according to a systematic review of randomized controlled trials.

All of these HCV inhibitors, as well as any other candidate agents, can be tested with the disclosed methods for their efficacy in inhibiting HCV genotype 3. The cells are then incubated at a suitable temperature for a period time to allow the replicons to replicate in the cells. The replicons can include a reporter gene such as luciferase and in such a case, at the end of the incubation period, the cells are assayed for luciferase activity as markers for replicon levels. Luciferase expression can be quantified using a commercial luciferase assay.

Alternately, efficacy of the HCV inhibitor can be measured by the expression or activity of the proteins encoded by the replicons. One example of such proteins is the NS3 protease, and detection of the protein expression or activity can be carried out with methods known in the art, e.g., Cheng et al., *Antimicrob Agents Chemother* 55:2197-205 (2011).

Luciferase or NS3 protease activity level is then converted into percentages relative to the levels in the controls which can be untreated or treated with an agent having known activity in inhibiting the HCV. A decrease in HCV replication or decrease in NS3 activity, as compared to an untreated control, indicates that the candidate agent is capable of inhibiting the corresponding genotype of the HCV. Likewise, a larger decrease in HCV replication or larger decrease in NS3 activity, as compared to a control agent, indicates that the candidate is more efficacious than the control agent.

EXAMPLES

The present disclosure is further defined by reference to the following examples. It will be apparent to those skilled in the art that many modifications, both to threads and methods, may be practiced without departing from the scope of the current disclosure.

Abbreviations

Unless otherwise stated all temperatures are in degrees Celsius (° C.). Also, in these examples and elsewhere, abbreviations have the following meanings:

| | |
|---|---|
| μF = | MicroFaraday |
| μg = | Microgram |
| μL = | Microliter |
| μM = | Micromolar |
| g = | Gram |
| hr = | Hour |
| mg = | Milligram |
| mL = | Milliliter |
| mM = | Millimolar |
| mmol = | Millimole |
| nM = | Nanomolar |
| nm = | Nanometer |
| pg = | pictograms |
| DMEM = | Dulbecco's modified Eagle's medium |
| EMCV = | encephalomyocarditis virus |
| FBS = | fetal bovine serum |
| HCV = | Hepatitis C virus |
| IRES = | internal ribosome entry site |
| rpm = | revolutions per minute |
| RT-PRC = | reverse transcription-polymerase chain reaction |

Example 1

Generation of Robust Genotype 3 Hepatitis C Virus Subgenomic Replicons

This example shows that adaptive mutations were identified from genotype 3 HCV viral replicons capable of replication in Huh7 cells and that HCV replicons with these adaptive mutations are useful tools for antiviral drug screening.

Materials and Methods

Cell Culture

Three HCV permissive cell lines were used during these studies: Huh7-Lunet, 51C, and 1C. Huh7-lunet was obtained from ReBLikon GmbH (Mainz, Germany) (Friebe et al., *J Virol* 79:380-92 (2005)). The derivation of 51C cells, and stable genotype 1a H77 and genotype 1b Con-1 Rluc-Neo replicon cells were previously described (see Robinson et al., *Antimicrob Agents Chemother* 54:3099-106 (2010)), 1C cells were derived by curing a GS-5885-resistant genotype 1a replicon clone derived from 51C cells (id.). GS-5885 is an NS5A inhibitor, available from Gilead Sciences, Inc., Foster City, Calif. This clonal line showed the highest permissivity to GT1a and 1b replicons out of screened 50 clones and was 5-10 folds more permissive than Huh7-Lunet and 51C cells overall. All cell lines were propagated in Dulbecco's modified Eagle's medium (DMEM) with GlutaMAX-I (Invitrogen, Carlsbad, Calif.) supplemented with 10% fetal bovine serum (FBS; HyClone, Logan, Utah), 1 unit/ml penicillin (Invitrogen), 1 μg/ml streptomycin (Invitrogen), and 0.1 mM non-essential amino acids (Invitrogen); this media formulation is referred to as complete DMEM. Replicon cell lines were selected and maintained in complete DMEM containing 0.5 mg/ml G418 (Geneticin; Invitrogen).

Construction of Plasmids Encoding Genotype 3a HCV Subgenomic Replicons

A plasmid (pGT3aS52SG) encoding a subgenomic genotype 3a replicon based on the S52 infectious clone (GenBank accession # GU814264) was prepared by DNA synthesis (GeneScript, Piscataway, N.J.) and cloning. The synthesized replicon incorporated following elements from 5' to 3' (FIG. 1): (1) the S52 5'UTR, extending to the first 48 nucleotides of core, (2) a linker with the nucleotide sequence, 5'-GGCGCGCCA-3' (SEQ ID NO: 1) which introduces the AscI restriction site (underlined), (3) the neomycin phosphotransferase II (neo) gene, (4) a linker with nucleotide sequence, 5'-GGCCGGCCGCGGCCGCAA-3' (SEQ ID NO: 2) which introduces FseI and Not I restriction sites (underlined), (5) the encephalomyocarditis virus (EMCV) IRES, (6) a linker with nucleotide sequence 5'-ACGCGTATG-3' (SEQ ID NO: 3) which introduces the MluI restriction site (underlined) and an ATG start codon for HCV polyprotein expression, (7) the NS3-NS5B polyprotein region of S52 including an NS5A adaptive mutation (S22041) and (8) the 3'UTR of S52. The synthetic DNA fragment encoding the S52 replicon was inserted into PUC19 between EcoRI and XbaI restriction sites.

Plasmid phRlucNeoSG2a was derived from the plasmid pLucNeo2a (Cheng et al., *Antimicrob Agents Chemother* 55:2197-205 (2011)). The hRenilla Luciferase-Neomycin fusion gene (hRluc-Neo) was PCR amplified from pF9 CMV hRluc-neo Flexi(R) (Promega, Madison, Wis.) by PCR using Accuprime Super Mix I (Invitrogen) and a primer set of AfeI hRLuc Fwd and NotI Neo Rev. These two primers had the following sequence and introduced restriction sites for subsequent cloning: AfeI hRLuc: 5' AT AGCGCTATGGCTTCCAAGGTGTACGA 3' (SEQ ID NO: 4, AfeI site underlined), NotI Neo Rev: 5' AAT GCGGCCGCTCAGAAGAACTCGTCA 3' (SEQ ID NO: 5, NotI site underlined). The hRluc-Neo amplification product was subcloned into pCR2.1-TOPO (Invitrogen). The resulting plasmid was digested with AfeI and NotI, and the excised fragment (hRluc-Neo) was ligated with T4 DNA ligase (Promega) into pLucNeo2a digested with the same enzymes. The resulting vector, phRlucNeoSG2a, was sequenced to ensure correct orientation and sequence of the hRluc-Neo fusion gene.

The subsequent PCR fragment was cut with AscI and MluI and gel purified using a commercial kit (Qiagen). The vector and insert pieces were ligated using LigaFast Rapid DNA Ligation System per manufacturer's protocol (Promega).

Construction of Mutant Replicons

Adaptive mutations were introduced into the replicon by site directed mutagenesis using a QuikChange Lightening kit (Stratagene, La Jolla, Calif.). All mutations were confirmed by DNA sequencing by TACGen (Hayward, Calif.).

RNA Transcription

Plasmids encoding genotype 3a subgenomic HCV replicons were linearized with XbaI and purified using a PCR purification kit (Qiagen). RNA was synthesized and purified with T7 MEGAScript (Ambion, Austin, Tex.) and RNeasy kits, respectively, according to the manufacturer's instructions. RNA concentrations were measured using optical density at 260 nm and confirmed by 0.8% agarose gel electrophoresis (Invitrogen).

RNA Transfection and Isolation of Stable Replicon Cell Lines

Ten micrograms of in vitro-transcribed RNA were transfected into Huh7-Lunet, 51C, or 1C cells by electroporation as previously described (Robinson et al., *Antimicrob Agents Chemother* 54:3099-106 (2010)). Briefly, cells were collected by trypsinization and centrifugation, then washed twice with ice-cold phosphate buffered saline (PBS) and resuspended in Opti-MEM medium (Invitrogen) at a concentration of $10^7$ cells/ml. Replicon RNA was added to 400 μl of cell suspension in a Gene Pulser (BioRad, Hercules, Calif.) cuvette (0.4-cm gap). Cells were electroporated at 270 V and 960 μF, incubated at room temperature for 10 minutes, resuspended in 30 ml complete DMEM and then plated into 100-mm-diameter dishes. Forty-eight hours after plating, medium was replaced with complete DMEM supplemented with 0.5 mg/ml G418 which was refreshed twice per week. Cell clones were isolated after approximately three weeks of G418 selection, expanded, and cryopreserved at early passages.

Replicon Colony Formation Assays

To determine the efficiency of G418-resistant colony formation, cells were electroporated with indicated amounts of replicon RNA or cellular RNA extract, and plated at multiple densities ranging from $2\times10^5$ to $2\times10^6$ cells/100 mm dish. Forty-eight hours after plating, medium was replaced with complete DMEM supplemented with 0.5 mg/ml G418 which was refreshed twice per week. Three weeks later, colony plates were used for cell expansion or G418-resistant foci were fixed with 4% formaldehyde and stained with 0.05% crystal violet in $H_2O$.

Extraction, Amplification, and Genotypic Analysis of HCV RNA

HCV RNA isolation, RT-PCR, and sequencing were performed by TACGen (Hayward, Calif.). HCV replicon cellular RNA was extracted and purified using an RNeasy kit (Qiagen) according to the manufacturer's protocol. RT-PCR was performed using the SuperScript III first-strand synthesis system (Invitrogen). PCR products were sequenced by TACGen (Hayward, Calif.).

Detection of NS5A Protein by Indirect Immunofluorescence

Replicon cells were plated in 96-well plates at a density of $1\times10^4$ cells per well. After cultured for 24 hours, cells were then stained for NS5A protein as described previously (Cheng et al., *Antimicrob Agents Chemother* 55:2197-205 (2011)). Briefly, cells were fixed in 4% paraformaldehyde for 20 minutes. Cells were then washed three times with PBS, blocked with 3% bovine serum albumin, 0.5% Triton X-100, and 10% FBS and then stained with anti-NS5A antibody. Staining was performed using a 1:10,000 dilution of mouse monoclonal antibody 9E10 (Apath, Brooklyn, N.Y.). After washing in PBS three times, a secondary anti-mouse antibody conjugated to Alexa Fluor 555 was used to detect anti-NS5A antibody labeled cells (Invitrogen). Nuclei were stained with 1 μg/ml Hoechst 33342 (Invitrogen). Cells were washed with PBS and imaged with a Zeiss fluorescence microscope (Zeiss, Thornwood, N.Y.).

Replicon Cell NS3 Protease Assay for Replicon RNA Replication

Genotype 3a clonal replicons cells were seeded in 96-well plates at a concentration of $1\times10^4$ cells per well. The cells were incubated for 24 hours, after which culture media were removed. The replicon cells were then lysed with 90 μl of 1× Promega luciferase lysis buffer supplemented with 150 mM NaCl at room temperature for 20 min on a plate shaker, 10 μl of 1 μM europium-labeled NS3 substrate in the above lysis buffer was added to each well. Protease activity data were collected and analyzed as previously described (Cheng et al., *Antimicrob Agents Chemother* 55:2197-205 (2011)).

Replicon Antiviral Assays 2,000 cells/well were seeded in 384-well plates in 90 μl of DMEM culture medium, excluding G418. Compounds were added to cells at a 1:225 dilution, achieving a final concentration of 0.44% in a total volume of 90.4 μl. Three-fold serial drug dilutions with 10 concentrations were used, and starting concentrations were 4.4 μM or 0.44 μM for all the tested compounds, except Compound A whose starting concentrations was 44.4 nM. Cell plates were incubated at 37° C. for 3 days, after which culture medium was removed and cells were assayed for luciferase activity as markers for replicon levels. Luciferase expression was quantified using a commercial luciferase assay (Promega). Luciferase or NS3 protease activity levels were converted into percentages relative to the levels in the untreated controls (defined as 100%), and data were fitted to the logistic dose response equation y_a/[1_(x/b)c] using XLFit4 software (IDBS, Emeryville, Calif.) (y is the amount of normalized luciferase signal, x is the drug concentration, a represents the curve's amplitude, b is the x value at its transition center [$EC_5$], and c is a parameter which defines its transition width).

Results

Adaptive Mutations

Using the methods similar to those for genotype 4, Huh7-Lunet cell colonies containing genotype 3 replicons were identified. Huh7-Lunet, 51C and 1C cells were transfected with the GT3a replicon RNA as described in the Materials and Methods. The numbers of surviving colonies were counted for each selection. The data represent the total number of colonies selected from at least 6 independent transfections in each cell line. Huh7-Lunet was obtained from ReB-Likon GmbH (Mainz, Germany). The derivation of 51C cells was previously described (Robinson et al., Agents Chemother 54:3099-106 (2010), 1C cells were derived by curing a GS-5885-resistant genotype 1a replicon clone derived from 51C cells. Transfection of Huh7-Lunet yielded two colonies that replicated the GT3a replicon and could subsequently be expanded into cell lines. Transfection of the other two cell lines did not yield any viable colonies (Table 1).

TABLE 1

Selection of stable GT3a replicon clones in Huh7-Lunet cells.

| Huh7-cell line | Lunet | 51C | 1C |
|---|---|---|---|
| Number of Colonies | 2 | 0 | 0 |

Total cellular RNA from 50000 GT3a replicon cells (expanded from a colony established in Huh7-Lunet cells described in Table 1) was extracted using a virus RNA QIAamp kit (Qiagen) as recommended by the manufacturer. Half of the total cellular RNA was then electroporated into Huh7-Lunet cells and the other half into 1C cells. Transfected cells were resuspended in complete DMEM medium and plated at a density of $1\times10^6$ and $3\times10^6$ cells in 150 mm-diameter dishes. Forty-eight hours after plating, medium was replaced with complete DMEM supplemented with 0.25 mg/ml G418 which was refreshed twice per week. Twenty five days later, colonies were counted from all the dishes and the sum is presented in Table 2 for each cell line. In vitro transcribed GT3a replicon RNA was transfected in parallel as a control. The replicon RNA extracted from the GT3a replicon cells clearly contained adaptations that greatly enhanced its colony formation efficiency compared to the original parental replicon.

TABLE 2

Selected GT3a replicon clones acquired adaptive genetic changes.

| Huh7-cell line | Lunet | 1C |
|---|---|---|
| In vitro transcribed GT3a RNA | 0 | 0 |
| Cellular RNA from GT3a replicon clone | 576 | 126 |

The selected GT3a replicon clone was expanded and subjected to genotypic analysis. Total cellular RNA was extracted and purified using a RNeasy kit (Qiagen). RT-PCR was performed using the SuperScript III first-strand synthesis system (Invitrogen). PCR products were sequenced by TAC-Gen (Hayward). The genotypic analysis identified the NS3 mutation N607S as an adaptive mutation (Table 3).

TABLE 3

A NS3 Mutation N607S identified in genotype 3a replicon cell line.

| Clone # | Mutation (NS3) |
|---|---|
| 2 | N607S |

Different classes of HCV inhibitors that target NS5A, NS5B active site, NS3 protease, NS5B non-active sites, NS4A and host factors, were evaluated for their antiviral activities against stable genotype 1b and genotype 3a Rluc-Neo replicon cells. Like in stable genotype 1b replicon cells, $EC_{50}$ values against genotype 3a replicon were generated successfully for all the inhibitors in a high throughput 384-well format by measuring NS3 protease activity.

Figure 2:
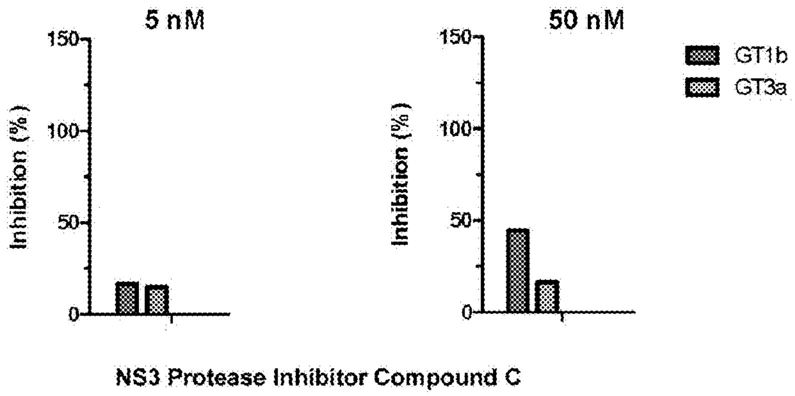
FIG. 2 presents data to show that the GT3a replicon NS3 protease activities in response to exposure to an NS3 protease inhibitor Compound C, $1\times10^5$ GT3a replicon cells were pelleted and lysed in 2.4 ml 1× Promega luciferase lysis buffer supplemented with 150 mM NaCl at room temperature for 15 min. The cell lysate was then distributed to a 96-well plate with a volume of 80 μl per well. Antiviral drug dilutions were prepared in DMSO at 10 times the final desired concentrations (5 nM or 50 nM). Portions (10 μl) of diluted Compound C was then added to each well of cell lysates, and the plates were incubated on a plate shaker for 10 minutes at room temperature. Then, 10 μl of 1 μM europium-labeled NS3 substrate was added to each well. Protease activity data were collected and the data were presented as the percentage of inhibition of DMSO control.
Figure 3:
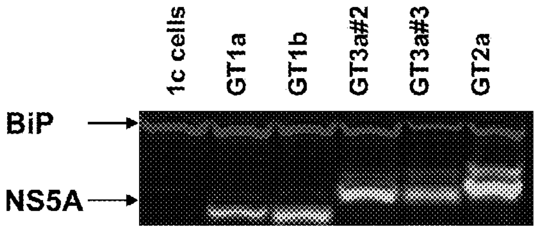
FIG. 3 shows robust NS5A expression in genotype 3a replicon cell line. Stable GT3a, GT1a, GT1b and GT2a replicon cells and 1C cells, $0.5\times10^6$ each were pelleted and completely lysed in 100 μl SDS loading buffer. Twelve microliter lysates were subjected to SOS-PAGE and Western blot analysis. The blot was stained with primary anti-NS5A antibody (Apath; 1:3000 dilution) and secondary anti-mouse antibody (IRDye 800CW Goat anti-Mouse IgG (H+L) from LI-COR, 1:10,000 dilution). The staining was then analyzed by Odyssey Imaging (LI-COR, Lincoln, Nebr.). The blot was also co-stained with anti-BiP antibody (Abcam, 1:1000 dilution) and secondary anti-rabbit antibody (IRDye 800CW Goat anti-Rabbit IgG (H+L) from LI-COR, 1:10,000 dilution) as a loading control, 1C cells were included as a negative control. Strong expression of NS5A was detected in the genotype 3a replicon cell clone, confirming that these cells stably and robustly replicate this replicon.

The data presented in Table 4 and FIG. 2-3 indicate that Compound B remained potent against genotype 3a replicon. However, Compound B lost 2.5-5 fold potency in comparison with its activities against genotype 1 b replicon. In contrast, Compound A had decreased activities against genotype 3a replicon >20000-fold respectively. Further, Compound D and Compound E lost their activities to a level below 4.44 μM. Compound C had decreased activities against genotype 3a replicon 58-fold than its genotype 1b activities.

These results demonstrate this novel genotype 3a replicon could serve as a valuable tool for drug discovery and lead compound optimization against HCV genotype 3a.

TABLE 4

Comparison of antiviral activities of HCV inhibitors against genotype 1b and 3a replicons

| Compounds | GT1b RLucNeo EC50 (nM) | GT3a RlucNeo EC50 (nM) |
|---|---|---|
| Compound A | 0.002 | >44.4 |
| Compound B | 117.3 | 281.1 |
| Compound C | 7.0 | 409.0 |
| Compound D | 0.47 | >4444.4 |
| Compound E | 0.55 | >4444.4 |

Here the Applicant reports the isolation of the first GT3a replicons that efficiently replicate in vitro. It is demonstrated that robust replication requires adaptive mutations. By incorporating adaptive mutations into luciferase encoding constructs, Applicant was able to generate GT3a replicon cell clones that will enable one to profile antiviral compounds. These replicon cells should also serve as valuable tools for molecular virology studies and the characterization of resistance mutations emerging in HCV genotype 3 patients.

In summary, subgenomic replicon cDNAs based on the genotype 3a S52 strain were synthesized, cloned, transcribed and electroporated into HCV permissive cell lines. Clonal cell lines stably replicating genotype 3a replicons were selected with G418. Adaptive mutations were identified by RT-PCR amplification and DNA sequencing and engineered into the parental replicons by site-directed mutagenesis.

Numerous electroporations into multiple different permissive cell lines allowed the identification of a few colonies that replicated either genotype 3 replicons. Expansion and sequencing of these replicons clones revealed adaptive mutations in viral proteins. One mutation identified so far was located in NS3 (N607S).

The establishment of robust genotype 3a replicon systems provides powerful tools to facilitate drug discovery and development efforts. Use of these novel replicons in conjunction with those derived from other genotypes will aid in the development of pan-genotypic HCV regimens.

Example 2

Screening of New HCV Inhibitors for Genotype 3

Example 1 shows that agents known to be HCV inhibitors for other genotypes, such as genotype 1, can be tested with the genotype 3 replicons for their efficacy in inhibiting genotype 3 HCV. It is also contemplated that agents not yet known to be inhibitory of HCV can be screened with these genotype 3 replicons as well.

The candidate HCV inhibitor can be a small molecule drug, a peptide or a protein such as antibodies, or nucleic acid-based such as siRNA. The candidate HCV inhibitor is incubated with cells that contain a genotype 3 replicon, at a suitable temperature for a period time to allow the replicons to replicate in the cells. The replicons can include a reporter gene such as luciferase and in such a case, at the end of the incubation period, the cells are assayed for luciferase activity as markers for replicon levels. Luciferase expression can be quantified using a commercial luciferase assay. Alternately, efficacy of the HCV inhibitor can be measured by the expression or activity of the proteins encoded by the replicons. One example of such proteins is the NS3 protease, and detection of the protein expression or activity can be carried out with methods known in the art, e.g., Cheng et al., *Antimicrob Agents Chemother* 55:2197-205 (2011).

Luciferase or NS3 protease activity level is then converted into percentages relative to the levels in the controls which can be untreated or treated with an agent having known activity in inhibiting the HCV. A decrease in HCV replication or decrease in NS3 activity, as compared to an untreated control, indicates that the candidate agent is capable of inhibiting the corresponding genotype of the HCV. Likewise, a larger decrease in HCV replication or larger decrease in NS3 activity, as compared to a control agent, indicates that the candidate is more efficacious than the control agent.

Example 3

Generation of Genotype 3a HCV Subgenomic Replicon's Containing a P89L Mutation This example describes the isolation of genotype 3a replicons that efficiently replicate in vitro. This study demonstrates that robust replication was achieved based on an adaptive mutation P89L in the NS3 protease domain, which could be further augmented by mutations in NS3, NS4A, and NS5A. By incorporating P89L into luciferase encoding constructs, this example generated stably replicating genotype 3a replicon cell lines, and by combing with selected host cells cured of genotype 3 replicons, efficient replication of genotype 3a HCV RNA was established in a transient-transfected cell culture. This system is fully capable of supporting potency profiling of antiviral compounds and selecting and phenotyping clinical resistance mutants emerging in HCV genotype 3 patients. These replicons should also serve as a valuable system for molecular virology studies of genotype 3 HCV, including a better understanding of its association with a high incidence of liver steatosis.

Materials and Methods

Cell Culture.

Huh7-Lunet cells were obtained from ReBLikon GmbH (Mainz, Germany) (Friebe et al., J Virol 2005; 79:380-92), 51C cells were derived by curing a Huh7-Lunet-based genotype 1a replicon clone and were described in Robinson et al., *Antimicrob Agents Chemother* 2010; 54:3099-106. 1C cells were derived by curing a GS-5885-resistant genotype 1a replicon clone derived from 51C cells, and showed much higher permissiveness to genotype 1a replicon replication. All cell lines were propagated in Dulbecco's modified Eagle's medium (DMEM) with GlutaMAX-I (Invitrogen, Carlsbad, Calif.) supplemented with 10% fetal bovine serum (FBS; HyClone, Logan, Utah), 1 unit/ml penicillin (Invitrogen), 1 μg/ml streptomycin (Invitrogen), and 0.1 mM non-essential amino acids (Invitrogen) (complete DMEM). Replicon cell lines were selected and maintained in complete DMEM containing 0.25 to 0.5 mg/ml G418 (Geneticin; Invitrogen).

Generation of Cured Cell Lines.

The cell lines GT3a-C1, GT3a-C2, and GT3a-C3 are 1C clones stably replicating the genotype 3a pGT3aS52SG-Neo replicon. To cure these cell lines of HCV RNA, they were cultured in the presence of IFN (1000 IU/ml), the NS5B nucleoside inhibitor 2'-CMeA (2 μM), the NS5A inhibitor BMS-790052 (500 nM), and the non-nucleoside NS5B inhibitor HCV-796 (1 μM). Cells were passaged in medium containing the four drugs twice a week for a total of eight passages. Cured cells were fully sensitive to G418 (500 mg/ml, also known as Geneticin®, an aminoglycoside antibiotic) and lacked detectable NS5A staining, confirming the absence of the replicon. Cured cell lines were expanded and cryopreserved at early passage levels. Cured cells were designated 3a-C1, 3a-C2, and 3a-C3.

Construction of Plasmids Encoding Genotype 3a HCV Subgenomic Replicons.

A plasmid (pGT3aS52NeoSG) encoding a subgenomic genotype 3a replicon based on the S52 infectious clone (GenBank accession #GU814263, SEQ ID NO: 12, which encodes polyprotein sequences provided in GenBank accession #ADF97231, SEQ ID NO: 13) was prepared by DNA synthesis (GeneScript, Piscataway, N.J.) and cloning. The synthesized replicon incorporated following elements from 5' to 3' (FIG. 4): (1) the S52 5'UTR (339 nt), plus the first 48 nucleotides of core, (2) a linker with the nucleotide sequence 5'-GGCGCGCCCA-3' (SEQ ID NO: 6), which introduces the AscI restriction site (underlined), (3) the neomycin phosphotransferase II (neo) gene, (4) a linker with nucleotide sequence 5'-GGCCGGCCA-3' (SEQ ID NO: 7), which introduces the FseI restriction site (underlined), (5) the encephalomyocarditis virus (EMCV) IRES, (6) a linker with nucleotide sequence 5'-ACGCGTATG-3' (SEQ ID NO: 3), which introduces the MluI restriction site (underlined) and an ATG start codon for HCV polyprotein expression, (7) the NS3-NS5B polyprotein region of S52 including an NS5A adaptive mutation (S2210I: equivalent to S2204I in genotype 1, or S232I within NS5A), and (8) the 3'UTR of S52 (235 nt). The synthetic DNA fragment encoding the S52 replicon was inserted into pUC57 between EcoRI and XbaI restriction sites.

A second plasmid (pGT3aS52RlucNeoSG) encoding a subgenomic replicon that incorporated the humanized Renilla luciferase (hRluc) reporter gene was generated as follows: The pGT3aS52NeoSG plasmid (described above) was cut using AscI and MluI restriction enzymes (to remove the neo gene) and gel purified using a commercial kit (Qiagen, Valencia, Calif.). A gene fragment encoding the hRluc gene fused with the neo gene along with the EMCV region from phRlucNeoSG2a plasmid (described below) were PCR amplified using Accuprime super mix I (Invitrogen) with the following primers: 2aRlucNeoAsclFor: 5'-AAC ACC ATC GGCGCGCCC ATG GCT TCC AAG GTG TAC GAC-3' (SEQ ID NO: 8, AscI site is introduced by the primer and is underlined), 2aEMCVIRESMluIRev: 5'-TCGGGG CCA TACGCGTAT CGT GTT TTT CAA AGG-3' (SEQ ID NO: 9, MluI site underlined). The subsequent PCR fragment was cut with AscI and MluI and gel purified using a commercial kit (Qiagen). The vector and insert pieces were ligated using the LigaFast Rapid DNA Ligation System per the manufacturer's protocol (Promega, Madison, Wis.). The resulting vector, pGT3aS52RlucNeoSG, was sequenced to confirm the correct orientation and sequence of the hRluc-Neo. The phRlucNeoSG2a plasmid was constructed by replacing the Luc-Neo fragment in the plasmid pLucNeoSG2a with the hRluc-Neo gene amplified from the plasmid hRluc-Neo Flexi(R) (Promega) as previously described (Robinson et al., *Antimicrob Agents Chemother* 2010; 54:3099-106 and Cheng et al., *Antimicrob Agents Chemother* 2011; 55:2197-205).

A third plasmid (P1-GT3aS52RlucSG), encoding a bicistronic replicon with the hRluc reporter gene downstream of the poliovirus IRES (PI) and the genotype 3a (S52 strain) HCV nonstructural genes (NS3-NS5B) downstream of the EMCV IRES was used for transient transfection studies. The plasmid was generated as follows: The pGT3aS52RlucNeoSG plasmid (described above) was cut using AscI and MluI restriction enzymes (to remove the Rluc-Neo gene) and gel purified using a commercial kit (Qiagen). A gene fragment encoding the PI, hRluc gene and EMCV region was PCR amplified from a genotype 1b plasmid (using Accuprime super mix I (Invitrogen) with the following primers: 3aPiRlucAscIFor: 5'-AAC ACC ATC GGCGCGCCA AAC CAA OTT CAA TAG-3' (SEQ ID NO: 10, AscI site is introduced by the primer and is underlined), 1bEMCVTRESMluIRev: 5'-TCG GGG CCA TACGCGTAT CGT GTT TTT CAA AGG-3' (SEQ ID NO: 11, MluI site underlined). The subsequent PCR fragment was cut with AscI and MluI and gel purified using a commercial kit (Qiagen). The vector and insert pieces were ligated using LigaFast Rapid DNA Ligation System per the manufacturer's protocol (Promega). The resulting vector, P1-GT3aS52RlucSG, was sequenced to confirm the correct orientation and sequence of the PI-hRluc region of the gene.

Construction of Mutant Replicons.

Adaptive mutations were introduced into the pGT3aS52RlucNeoSG or Pi-Rluc-GT3aS52 replicons by site-directed mutagenesis using a QuikChange Lightening kit (Stratagene, La Jolla, Calif.). All mutations were confirmed by DNA sequencing by TACGen (Hayward, Calif.).

RNA Transcription.

Plasmids encoding genotype 3a subgenomic HCV replicons were linearized with XbaI and purified using a PCR purification kit (Qiagen). RNA was synthesized and purified with T7 MEGAScript (Ambion, Austin, Tex.) and RNeasy kits (Qiagen), respectively, according to the manufacturer's instructions. RNA concentrations were measured using optical density at 260 nm and confirmed by 0.8% agarose gel electrophoresis (Invitrogen).

RNA Transfection and Isolation of Stable Replicon Cell Lines.

Ten micrograms of in vitro-transcribed RNA were transfected into Huh7-Lunet or 1C cells by electroporation as previously described (Robinson et al., *Antimicrob Agents Chemother* 2010; 54:3099-106). Briefly, cells were collected by trypsinization and centrifugation, then washed twice with ice-cold phosphate buffered saline (PBS) and resuspended in Opti-MEM medium (Invitrogen) at a concentration of $10^7$ cells/ml. Replicon RNA was added to 400 μl of cell suspension in a Gene Pulser (BioRad, Hercules, Calif.) cuvette (0.4-cm gap). Cells were electroporated at 270 V and 960 μF, incubated at room temperature for 10 minutes, resuspended in 30 ml complete DMEM and then plated into two 100-mm-diameter dishes. Forty-eight hours after plating, medium was replaced with complete DMEM supplemented with 0.25 mg/ml G418, which was refreshed twice per week. After three weeks, cell clones were isolated, expanded with 0.5 mg/ml G418, and cryopreserved at early passages.

Replicon Colony Formation Assays.

To determine the efficiency of G418-resistant colony formation, cells were electroporated with the indicated amounts of replicon RNA or extracted cellular RNA, and plated at multiple densities ranging from $2\times10^5$ to $2\times10^6$ cells/100-mm dish. Forty-eight hours after plating, media were replaced with complete DMEM supplemented with 0.5 mg/ml G418, which was refreshed twice per week. Three weeks later, colony plates were used for cell expansion or G418-resistant foci were fixed with 4% formaldehyde and stained with 0.05% crystal violet.

Extraction, Amplification, and Genotypic Analysis of HCV RNA.

HCV RNA isolation, RT-PCR, and population sequencing were performed by TACGen. Briefly, HCV replicon cellular RNA were extracted and purified using an RNeasy kit (Qiagen) according to the manufacturer's protocol. RT-PCR was performed using the SuperScript III first-strand synthesis system (Invitrogen), and PCR products were subsequently sequenced by TACGen.

Detection of NS5A Protein by Indirect Immunofluorescence.

Replicon cells were plated in 96-well plates at a density of $1\times10^4$ cells per well. After incubation for 24 hours, cells were then stained for NS5A protein as described previously (Cheng et al., *Antimicrob Agents Chemother* 2011; 55:2197-205). Briefly, cells were fixed in 4% paraformaldehyde for 20 minutes. Cells were then washed three times with PBS, blocked with 3% bovine serum albumin, 0.5% Triton X-100, and 10% FBS and stained with anti-NS5A antibody. Staining was performed using a 1:10,000 dilution of mouse monoclonal antibody 9E10 (Apath, Brooklyn, N.Y.). After washing in PBS three times, a secondary anti-mouse antibody conjugated to Alexa Fluor 555 was used to detect anti-NS5A antibody labeled cells (Invitrogen). Nuclei were stained with 1 μg/ml Hoechst 33342 (Invitrogen). Cells were washed with PBS and imaged with a Zeiss fluorescence microscope (Zeiss, Thornwood, N.Y.).

Detection of NS5A Protein by Western Blot.

The stable GT3a replicon clones and pooled cell line, as well as GT1b replicon cells, were pelleted and lysed in SDS loading buffer. Lysates were then subjected to SDS-PAGE and Western blot analysis. The blot was stained with primary anti-NS5A antibody (Apath; 1:3000 dilution) and secondary anti-mouse antibody (IRDye 800CW Goat anti-Mouse IgG (H+L) from LI-COR [Lincoln, Nebr.], 1:10,000 dilution). The blot was also co-stained with anti-BiP antibody (Abcam, 1:1000 dilution) and secondary anti-rabbit antibody (IRDye 800CW Goat anti-Rabbit IgG (H+L) from LI-COR, 1:10,000 dilution) as a loading control. Staining was analyzed by Odyssey Imaging (LI-COR).

Replicon Antiviral Assays.

Replicon RNA were electroporated into 1C cells as described above. After transfection, cells were quickly transferred into 100 mL of pre-warmed culture medium, and 90 μl was seeded in 384-well plates at a density of 2,000 cells/well. Cells were treated with three-fold serial drug dilutions at 10 different concentrations. Cell plates were incubated at 37° C. for 3 days, after which culture medium was removed and cells were assayed for luciferase activity as markers for replicon levels. Luciferase expression was quantified using a commercial luciferase assay (Promega). Luciferase levels were converted into percentages relative to the levels in the untreated controls (defined as 100%), and data were fitted to the logistic dose-response equation $y=a/[1+(x/b)^c]$ using XLFit4 software (IDBS, Emeryville, Calif.).

Antiviral Compounds.

VX-950 (telaprevir), boceprevir, and 2-C-methyl adenosine (2-CMeA) were purchased from Acme Bioscience (Belmont, Calif.). Cyclosporine A (CsA) was purchased from Sigma-Aldrich (St. Louis, Mo.). The Wyeth HCV NS5B site IV inhibitor HCV-796 was synthesized by Curragh Chemistries (Cleveland, Ohio). Gilead compounds GS-5885, GS-9190, GS-9451, GS-9669, and GS-7977, Pfizer NS5B thumb site II inhibitor filibuvir, Merck NS5B thumb site I inhibitor MK-3281 and protease inhibitor MK-5172, and the Bristol-Myers Squibb NS5A inhibitor (BMS-790052) were synthesized by Gilead Sciences.

Results

Construction of a Subgenomic Genotype 3a Replicon and Colony Formation in Permissive Huh-7 Clones.

Figure 4:
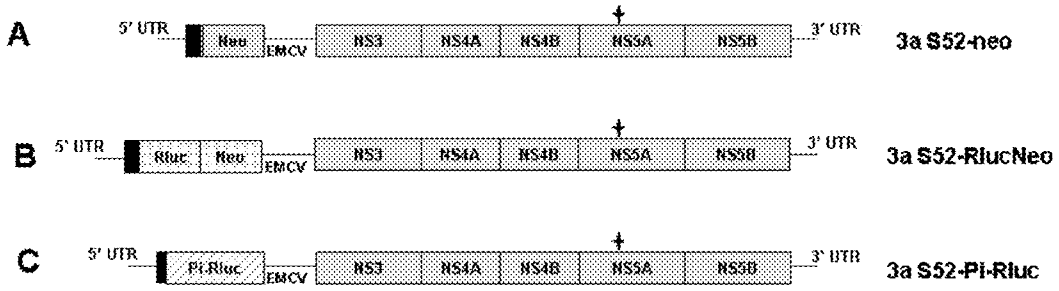
FIG. 4A-C show a schematic diagram of genotype 3a replicon constructs in Example 3. Genotype 3a S52 strain replicons encode a neomycin phosphotransferase II gene (neo) (A), a Renilla luciferase (Rluc)-neo fusion reporter (B) or a Pi Renilla luciferase (PiRluc) fusion reporter (C). The synthesized replicon incorporated following elements from 5' to 3': the S52 5'UTR; the Neo, Rluc-neo or Pi-Rluc reporter gene; the EMCV IRES; the NS3-NS5B polyprotein region of S52 including an NS5A adaptive mutation (522101) and the 3'UTR of S52. ■ indicates HCV S52 core sequence. ▒ indicates HCV polyprotein sequence. "+" indicates the S2210I adaptive mutation. The 5' and 3' non-translated regions (NTR) and EMCV IRES are indicated.

A subgenomic genotype 3a replicon was constructed as previously described by Lohmann et al., *Science* 1999; 285: 110-3 and based on the consensus sequence (GenBank accession #GU814263) of the genotype 3a S52 strain (FIG. 4). The S52 strain was selected due to its robust infection in chimpanzees. To enhance the basal level of replication, an NS5A mutation S2210I (equivalent to S2204I in genotype 1a) was incorporated.

In vitro-transcribed replicon RNA was electroporated into Huh7-Lunet, 51C, or 1C cells. In Huh7-Lunet cells, no stable replicon colony emerged after six attempts of transfection each with 10 μg of RNA (Table 5). Similar results were also seen in 51C cells that were selected by curing a genotype 1a replicon clone derived from Huh7-Lunet cells, indicating a very low colony formation efficiency of genotype 3a replicons in these two highly genotype 1 replicon-permissive cell lines. In contrast, in 1C cells that were selected by curing a GS-5885-resistant genotype 1a replicon clone derived from 51C cells, three stable colonies could be selected from five transfections (Table 5). This result suggests that although genotype 3 HCV has a very low replication efficiency in cell culture, the 1C cells that showed higher permissiveness to genotype 1a replicon replication than 51C and Huh7-Lunet cells provide better support to genotype 3 HCV replication and permit establishment of stable G418-resistant colonies.

TABLE 5

1C cells are more permissive than Huh7-Lunet cells to GT3a replicon replication

| Huh-7 cell lines | Huh7-Lunet | 51C | 1C |
|---|---|---|---|
| Number of transfections | 6 | 4 | 5 |
| Number of total surviving clonies | 0 | 0 | 3 |

Huh7-Lunet, 51C and 1C cells were transfected with genotype 3a replicon RNA. The number of surviving colonies was counted for each selection transfected with 10 μg RNA.

Characterization of Stable Genotype 3a Replicon Clones.

Figure 5:
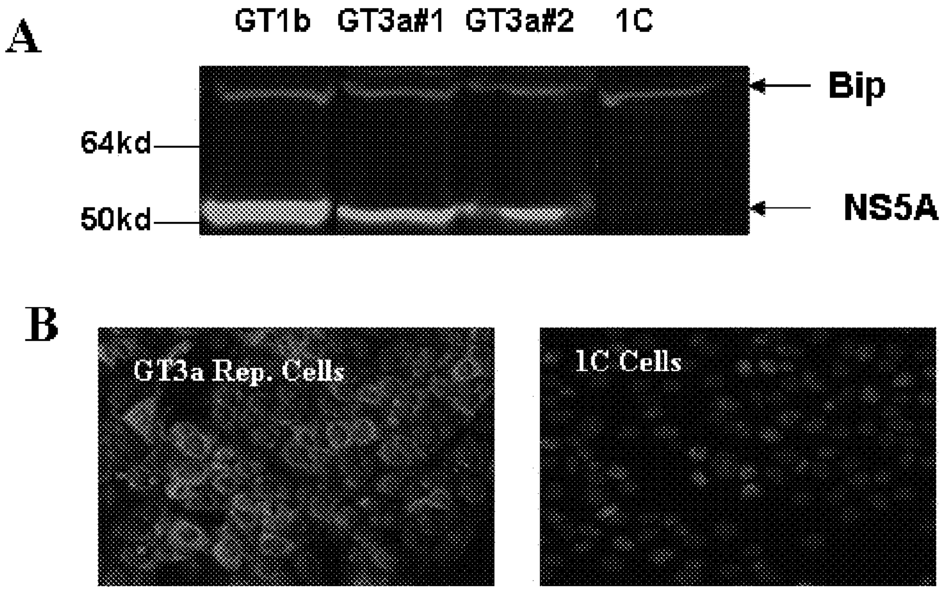
FIG. 5A-B show NS5A expression in selected genotype 3a replicon cells. (A). NS5A expression in selected replicon cells. The two stable genotype 3a replicon clones, as well as the genotype 1b replicon cells, were pelleted and completely lysed in SDS loading buffer. Lysates were then subjected to SDS-PAGE and Western blot analysis. The blot was stained with primary anti-NS5A antibody (Apath; 1:3000 dilution) and secondary anti-mouse antibody (IRDye 800CW Goat anti-Mouse IgG (H+L) from LI-COR, 1:10,000 dilution). The blot was also co-stained with anti-BiP antibody (Abcam, 1:1000 dilution) and secondary anti-rabbit antibody (IRDye 680CW Goat anti-Rabbit IgG (H+L) from LI-COR, 1:10,000 dilution) as a loading control. The staining was analyzed by Odyssey Imaging (LI-COR). (B). NS5A immunostaining of the selected replicon cells. The genotype 3a replicon clone #1 was stained with anti-NS5A antibody (red) and Hoechst 33342 (blue, indicating nuclei), 1C cells were stained as a negative control.

To confirm that the selected colonies harbored replicating genotype 3a replicons, an immunohistochemical and Western analysis were performed. The stable genotype 3a replicon cell lines were lysed in SDS loading buffer and analyzed by Western blot. An anti-NS5A antibody readily detected NS5A protein in all three genotype 3a replicon cell lines at levels only slightly lower than those in the genotype 1b replicon cell line (FIG. 5A; data not shown for genotype 3a #3 clone that was isolated and analyzed later). Similar to genotype 1b, only the p56 form of NS5A protein was detected in these replicon clones, likely due to the presence of a S2210I (equivalent to S2204I in genotype 1) mutation in the NS5A protein. Furthermore, an immunohistochemical analysis of the genotype 3a replicon cell line using anti-NS5A antibody confirmed the expected expression pattern for NS5A, particularly in the perinuclear region. In contrast, untransfected parental 1C cells did not show detectable NS5A protein (FIG. 5B).

Figure 6:
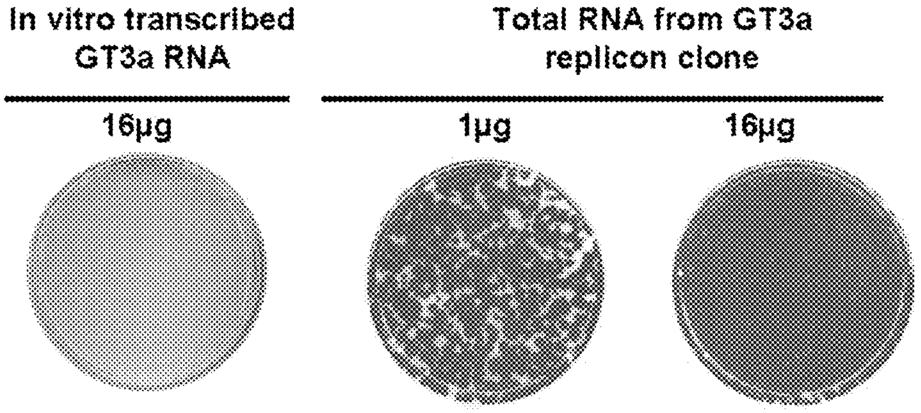
FIG. 6 shows that selected genotype 3a replicon clone acquires adaptive mutations. Total cellular RNA was extracted from the genotype 3a replicon cell clone #1 and then electroporated into Huh7-Lunet cells at the indicated amounts. Transfected cells were resuspended in complete DMEM medium, plated in a 100-mm diameter dish, and cultured with 0.5 mg/ml G418 (also known as Geneticin®, an aminoglycoside antibiotic). Three weeks later, colony plates were fixed with 4% formaldehyde and stained with 0.05% crystal violet. In vitro-transcribed GT3a replicon RNA was transfected in parallel as a control.

The very low colony formation efficiency of genotype 3a replicon RNA, even in 1C cells, suggests that adaptive mutations may have been acquired in the colonies that did emerge. To investigate whether there were adaptive changes in viral genomes in genotype 3a replicon colonies, total cellular RNA was extracted from the genotype 3a replicon clone #1 and re-electroporated into naive Huh7-Lunet cells. Transfected cells were then cultured in the presence of G418, and colony formation was monitored. In vitro-transcribed genotype 3a replicon RNA was transfected in parallel for comparison. Consistent with the data in Table 5, 16 μg of parental replicon RNA did not yield a viable colony in Lunet cells. In contrast, transfection of 1 total cellular RNA extracted from the genotype 3 cell line, only a small fraction of which was HCV RNA, yielded more than >200 colonies (FIG. 6). Similar results were also seen with replicon clones #2 and #3 (data not shown). These results confirm that the selected genotype 3a replicon clones acquired adaptive mutation(s) and became capable of replicating efficiently in vitro.

Genotypic Analyses of Genotype 3a Replicon Clones.

To identify adaptive mutations, genotype 3a replicon clones were subjected to genotypic analyses. Total cellular RNA was extracted, and HCV replicon RNA was subsequently amplified by RT-PCR. PCR products that cover the entire NS3-NS5B region were sequenced by population sequencing. Amino acid changes in each clone are summarized in Table 2. All clones had an amino acid substitution of leucine with proline at residual position 89 (P89L) within the viral NS3 protease domain. Clone #3 had an additional mutation, Q41R, that was also located in the NS3 protease domain. A number of individual clones or pools were also selected from the total cellular RNA retransfection study shown in FIG. 6 and were analyzed for genotypic changes. Although a number of mutations were identified in individual clones and distributed throughout viral NS3, NS4A, NS4B, or NS5A proteins, they all appeared in conjunction with P89L (Table 7). These results indicate that P89L serves as a primary adaptive mutation for HCV genotype 3 RNA replication in cell culture.

TABLE 6

Mutations identified in GT3a replicon cells lines

| Clone # | NS3 |
|---|---|
| 1 | P89L |
| 2 | P89L |
| 3 | P89L and Q41R |

TABLE 7

Mutations identified in genotype 3a-neo replicon cells lines

| | Mutations | | | |
|---|---|---|---|---|
| Clones | NS3 | NS4A | NS4B | NS5A |
| 1C-GT3a#1 | P89L | — | — | — |
| 1C-GT3a#1-RL#pool | P89L/A379V/K583E | — | — | — |
| 1C-GT3a#1-RL#1 | Q41R/P89L/R587Q | — | — | — |
| 1C-GT3a#1-RL#2 | P89L/A166T | A15V | — | — |
| 1C-GT3a#1-RL#3 | P89L/A166T | A15V | — | — |
| 1C-GT3a#1-RL#4 | P89L/A166T | — | — | — |
| 1C-GT3a#2 | P89L | — | — | — |
| 1C-GT3a#2-RC#9 | P89L/P194L/A380N | — | — | — |
| 1C-GT3a#2-RC#12 | P89L | V38I | — | — |
| 1C-GT3a#2-RC#15 | P89L/A379V | S1C | — | — |
| 1C-GT3a#2-RC#16 | P89L | — | I35T/I131M | V441A |
| 1C-GT3a#2-RC#17 | P89L/K371R/K583E | — | — | S62T |
| 1C-GT3a#2-RC#18 | P89L/S548L/Y502Y | — | H108Q | V450A |
| 1C-GT3a#2-RC#pool | P89L | — | — | — |
| 1C-GT3a#3 | Q41R/P89L | — | — | — |
| 1C-GT3a#3-RL-pool | Q41R/P89L | — | — | — |

Generation of Cell Lines Stably Replicating Luciferase-Encoding Genotype 3a Replicons.

Figure 7:
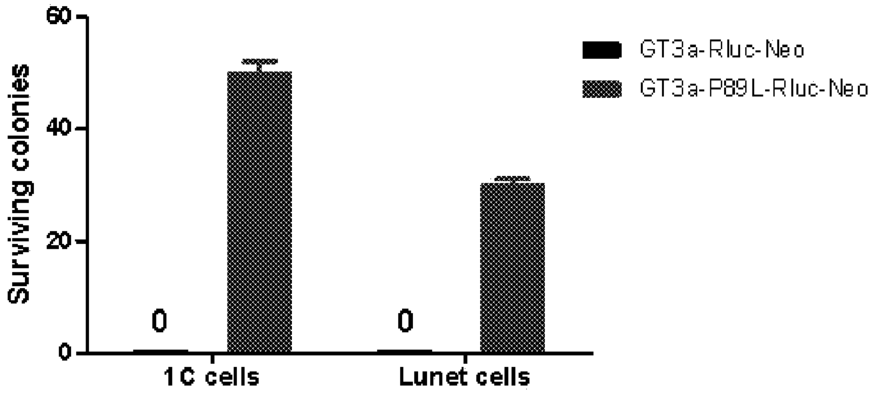
FIG. 7 is a chart showing the establishment of stable and robust GT3a Rluc-Neo replicon cell lines. The P89L mutation in NS3 was introduced into the GT3a S52 Rluc-neo construct by site-directed mutagenesis. The GT3a-P89L-Rluc-neo mutant replicon RNA and the parental GT3a-Rlu-neo replicon RNAs (10 μg each) were transfected into 1C or Huh7-Lunet cells. The number of surviving colonies was counted for each selection.

To investigate whether emerging mutations enhanced replicon replication, the mutation P89L in NS3 was introduced into the parental genotype 3a replicon sequence (FIG. 4). To facilitate measurement of replication in cell culture, the Neo gene in the parental genotype 3a replicon construct (FIG. 4A) was replaced with a Renilla luciferase (Rluc)-neo fusion reporter as shown in FIG. 4B. Huh7-Lunet or 1C cells were transfected with Rluc-neo replicon RNA encoding the adaptive mutation P89L in NS3 and were cultured in the presence G418. In parallel, parental genotype 3a neo and Rluc-neo constructs were also transfected and selected in Huh7-Lunet or 1C cells. Consistent with the results in Table 1, the Neo replicon yielded an average of one colony per selection in 1C cells and no colony in Huh7-Lunet cells (FIG. 7). Interestingly, the Rluc-neo replicon without adaptive mutations failed to yield any colonies after G418 selection in either cell line, probably due to the insertion of the large luciferase sequence into the replicon. In contrast, introduction of the mutation P89L dramatically improved genotype 3a Rluc-neo colony formation efficiency and led to an average of 30 or 50 colonies per selection in Huh7-Lunet and 1C cells respectively (FIG. 7). These data confirm that the mutation P89L is a genotype 3a adaptive mutation.

Figure 8:
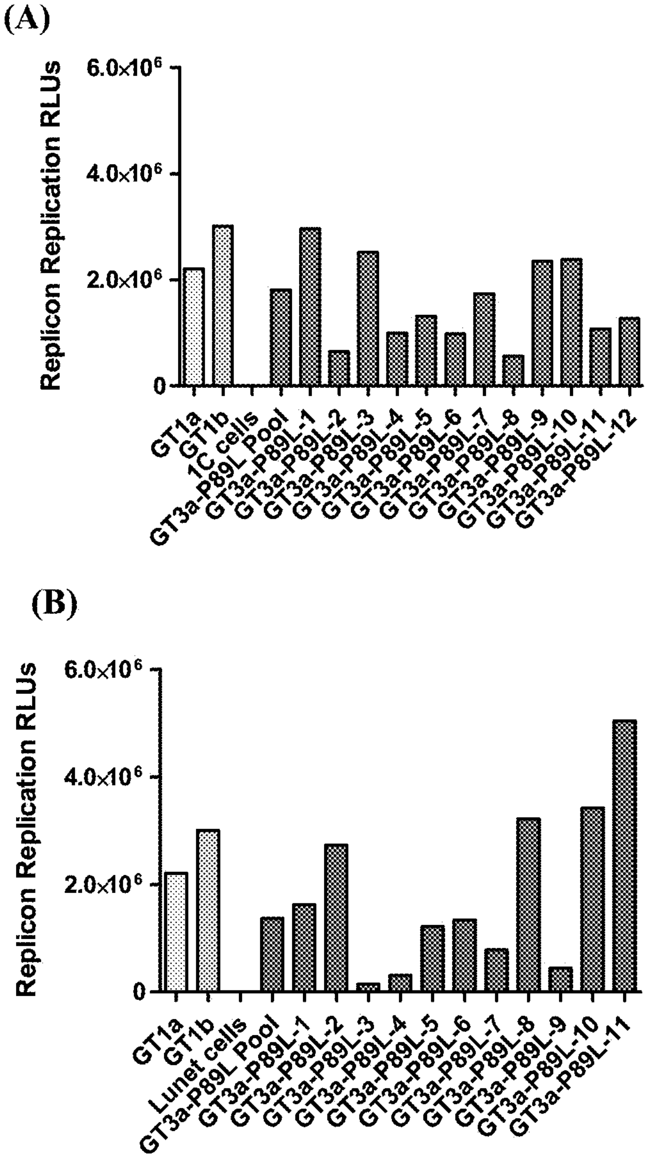
FIG. 8A-B indicate Luciferase expression in genotype 3a luciferase cell clones. (A). Selected genotype 3a replicon cell clones derived from 1C cells. (B). Selected genotype 3a replicon cell clones derived from Huh7-Lunet cells. Genotype 1a and genotype 1b stable replicon cells were included as references. Untransfected 1C or Huh7-Lunet cells were included as a negative control, 60,000 cells were used for renilla luciferase activity assay.

To further characterize these stably replicating replicon clones, 12 individual Rluc-neo replicon colonies and a colony pool from Huh7-Lunet and 1C cells were isolated and expanded. Luciferase activity was used to assess replication levels in these stable genotype 3a Rluc replicon cell lines. As shown in FIG. 8, the pooled cell line and essentially all the isolated clones from either Huh7-Lunet or 1C cells showed comparable or slightly less (<5-fold) luciferase activity compared with the highly adapted genotype 1a or 1b replicons, suggesting an efficient replication of genotype HCV 3a in cell culture. The high efficiency of and slight variation in HCV RNA replication among the replicon clones were further verified by immunohistochemical analysis of NS5A protein expression (data not shown). Genotypic analyses confirmed the presence of P89L in all the pools and clonal cells. Additional mutations such as A166K or K583E in viral NS3 protein were identified but were not necessary for replication and only occurred in half of isolated clones (Table 8). Put together, these data demonstrate that a P89L substitution in NS3 protease domain significantly stimulates genotype 3a HCV replication and allows establishment of stably replicating luciferase-encoding genotype 3a replicons.

TABLE 8

Mutations identified in GT3a-P89L-Rluc-neo replicon cells lines

| | Mutations | | | |
|---|---|---|---|---|
| Clones | NS3 | NS4A | NS4B | NS5A |
| GT3a-Rluc-Neo-P89L-1C-pool | P89L/A166A (major), S, T mix | — | — | — |
| GT3a-Rluc-Neo-P89L-C1 | P89L | — | — | — |

TABLE 8-continued

Mutations identified in GT3a-P89L-Rluc-neo replicon cells lines

| Clones | Mutations NS3 | NS4A | NS4B | NS5A |
|---|---|---|---|---|
| GT3a-Rluc-Neo-P89L-C2 | P89L/S534G | — | — | — |
| GT3a-Rluc-Neo-P89L-C3 | P89L | — | — | — |
| GT3a-Rluc-Neo-P89L-C4 | P89L | S1C | — | — |
| GT3a-Rluc-Neo-P89L-C5 | P89L | — | — | — |
| GT3a-Rluc-Neo-P89L-C6 | P89L | — | — | — |
| GT3a-Rluc-Neo-P89L-C7 | P89L/V511A | — | — | — |
| GT3a-Rluc-Neo-P89L-C8 | P89L/Q34H | — | — | — |
| GT3a-Rluc-Neo-P89L-C9 | P89L | — | — | — |
| GT3a-Rluc-Neo-P89L-C10 | P89L/T403I | — | — | E412G |
| GT3a-Rluc-Neo-P89L-C11 | P89L | — | — | — |
| GT3a-Rluc-Neo-P89L-C2 | P89L/A98V (A) | M51I (M) | A127T (A) | — |
| GT3a-Rluc-Neo-P89L-LP | P89L/K583E(K) | — | — | — |
| GT3a-Rluc-Neo-P89L-L1 | P89L | — | — | S103A |
| GT3a-Rluc-Neo-P89L-L2 | P89L/Q34H/K380N | — | — | — |
| GT3a-Rluc-Neo-P89L-L3 | P89L/Q41R | — | — | — |
| GT3a-Rluc-Neo-P89L-L4 | P89L | — | — | — |
| GT3a-Rluc-Neo-P89L-L5 | P89L | — | — | — |
| GT3a-Rluc-Neo-P89L-L6 | P89L | — | — | — |
| GT3a-Rluc-Neo-P89L-L7 | P89L/A166T | — | — | — |
| GT3a-Rluc-Neo-P89L-L8 | P89L/A379T | — | — | C451R |
| GT3a-Rluc-Neo-P89L-L9 | P89L | — | — | — |
| GT3a-Rluc-Neo-P89L-L10 | P89L | — | — | — |
| GT3a-Rluc-Neo-P89L-L11 | P89L/K583E | — | — | — |
| GT3a-Rluc-Neo-P89L-L12 | P89LA379T | — | — | — |

Generation of Transient-Transfection Replicating Luciferase-Encoding Genotype 3a Replicons.

Figure 9:
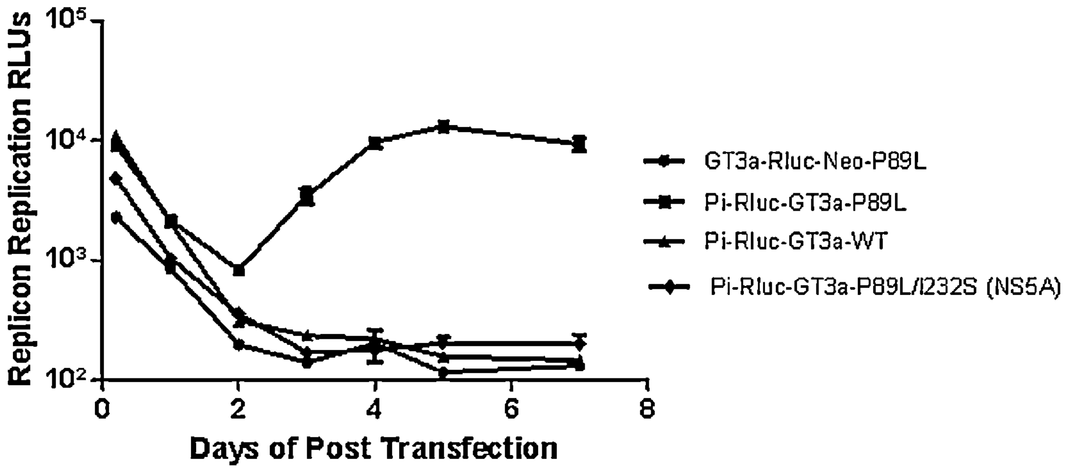
FIG. 9 shows that combined mutations P89L in NS3 and S232I in NS5A (S2210I) enhanced genotype 3a replicon replication. Mutations P89L in NS3 and double mutations P89L in NS3 and S232I in NS5A were introduced into genotype 3a S52 PiRluc construct by site-directed mutagenesis respectively. All replicon RNAs were transfected into 1C cells individually and $1\times10^4$ transfected cells were plated into wells in a 96-well plate. At 4 hours, and day 1 to day 7 post transfection, cells were analyzed for Renilla luciferase activity.

To facilitate measurement of replication efficiency and kinetics of genotype 3a replicon in antiviral activity assays and clinical resistance studies, the Rluc-Neo gene in the parental GT3a-Rluc-Neo replicon construct (FIG. 4B) was replaced with a bicistronic replicon encoding the Rluc reporter gene downstream of the poliovirus IRES (FIG. 4C). Following transfection of GT3a-Rluc-Neo-P89L and Pi-Rluc-GT3a-P89L into 1C cells, luciferase activity was measured post transfection at 4 hours and daily for 7 days. As shown in FIG. 9, luciferase activity of the Rluc-Neo-GT3a-P89L replicon continuously decreased to a level slightly above the background (~100 relative luminescence units (RLU)), suggesting the replicon did not replicate efficiently in the transient assay, likely due to insertion of the large-size Rluc-Neo gene. Pi-Rluc-GT3a-P89L conferred a meaningfully higher level of replication. After an initial dip in luciferase activity over the first 2 days post transfection due to input RNA degradation, HCV RNA replication reached a level that was two orders of magnitude higher than that achieved with Rluc-Neo-GT3a-P89L. These results indicate that the Pi-Rluc-GT3a-P89L replicon is a useful tool to measure the replication efficiency and kinetics of a genotype 3a replicon.

Using the transient-transfection tool, we determined whether the mutation S2210I (equivalent to S2204I in genotype 1) in viral NS5A protein is necessary for genotype 3a RNA replication in combination with P89L. The mutation S2210I in the Pi-Rluc-GT3a-P89L replicon was reverted by substituting isoleucine with serine, and the resulting replicon construct was transfected into 1C cells. In the absence of S2210I, replicon viral RNA levels did not increase, and the replicon did not replicate during 7 days post transfection (FIG. 9). This result indicates that the NS5A mutation S2210I is required by the adaptive mutation P89L to support efficient genotype 3a replicon replication.

Establishment of Highly Permissive Cell Lines to Improve Genotype 3a HCV RNA Replication.

Figure 10:
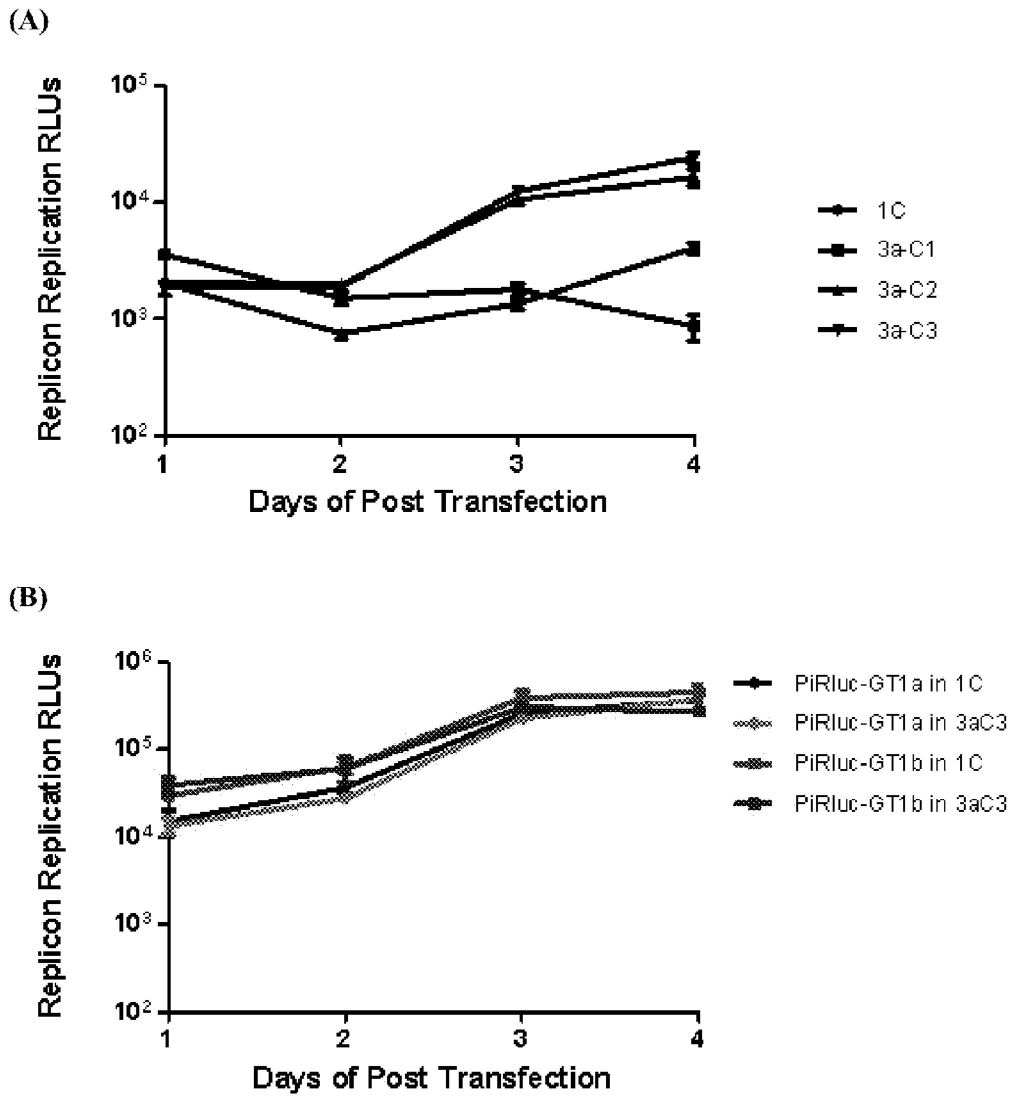
FIG. 10A-B present curves to show that the genotype 3a cured cell lines are highly permissive to genotype 3a replication. Pi-Rluc-GT3a-P89L (A), Pi-Rluc-GT1a and Pi-Rluc-GT1b (B) replicon RNAs were transfected into 1C or genotype 3a cured cells. Luciferase activity was measured daily for 4 days post transfection. Two cured replicon cell lines, 3a-C2 and 3a-C3, exhibited the highest degree of permissiveness to genotype 3a replication.

Although replication of Pi-Rluc-GT3a-P89L can be readily measured in a transient transfection assay, it is not robust enough for the high-throughput assays used for drug discovery and development research. Two approaches were taken to further improve replication efficiency. The first approach was to establish more permissive cell lines to support genotype 3 RNA replication. We cured the three stable clones selected with the parental genotype 3a neo replicon (Table 5) and speculated that these clonal cells might be unique to genotype 3a replication because of the low frequency of selection. The three replicon cell lines (Table 6) were cured using a high-dose cocktail of IFN and three direct antivirals for 4 weeks. The resulting cured cell lines, designated 3a-C1, 3a-C2, and 3a-C3, lacked detectable HCV replication. To assess the ability of the cured cell lines to support genotype 3a replication, they were transfected with the Pi-Rluc-GT3a-P89L replicon, and luciferase activity was measured daily for 4 days. Importantly, two cured replicon clones, 3a-C2 and 3a-C3 but not 3a-C1, exhibited approximately 10-fold higher permissiveness to genotype 3a replication than 1C cells (FIG. 10A). To determine whether the cured cell lines also showed higher permissiveness to other HCV genotype replication, genotype 1a and 1b replicons were transfected into 1C and the 3a-C3 cell lines. Interestingly, there was no notable difference of genotype 1a and 1b replicon replication between 1C cells and the cured cell line (FIG. 10B). These results thus indicated that cell lines, like 3a-C3 cell, was successfully established that could support significantly higher replication, specifically to genotype 3 HCV.

Characterization of Secondary Adaptive Mutations to Improve Genotype 3a HCV RNA Replication.

Figure 11:
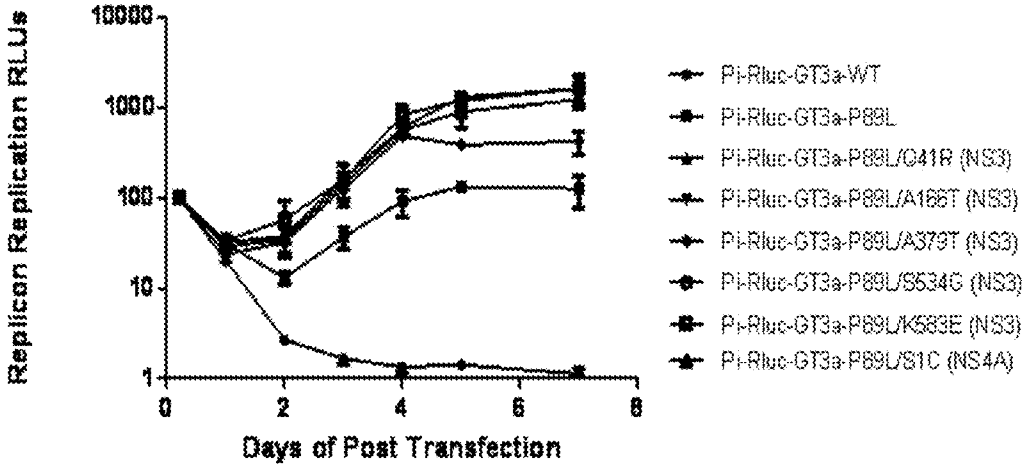
FIG. 11A-B show that secondary mutations in NS3 or NS4A enhanced genotype 3a replicon replication. Secondary mutations Q41R, A166T, A379T, S534G, K583E in NS3, or SIC, in NS4A were introduced into the GT3a-P89L PiRluc construct by site-directed mutagenesis. Replicon RNAs (Pi-Rluc-GT1b as a control) were individually transfected into 1C (A) or 3a-C3 (B) cured cells, and $1\times10^4$ transfected cells were plated per well in a 96-well plate. Cells were analyzed for renilla luciferase activity at 4 hours and daily for 7 days post transfection. Data presented in the figure are from a representative experiment of at least two independent experiments.
Figure 11:
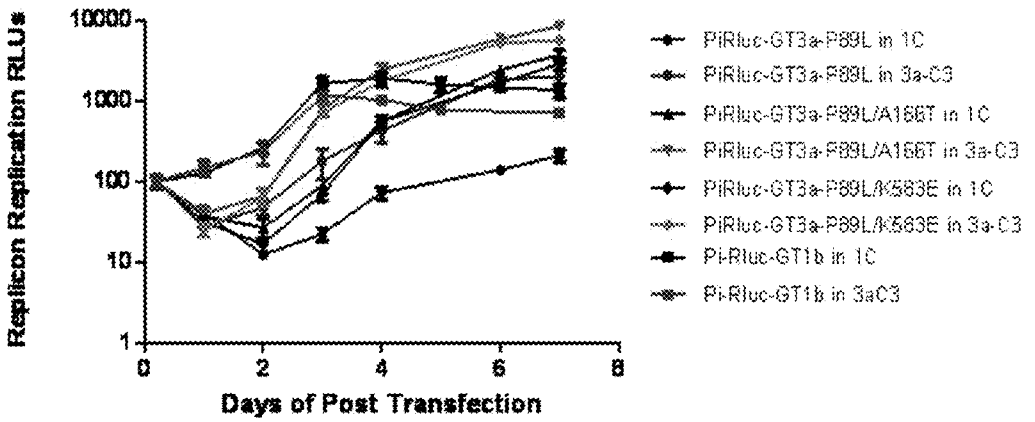

The second approach was to identify secondary adaptive mutations that further augmented genotype 3 HCV replication. A number of additional mutations were identified in combination with P89L (summarized in Tables 7 and 8). To determine whether those mutations could further enhance P89L-dependent HCV RNA replication, 6 individual mutations that emerged at least twice in those stable clones were selected and introduced into Pi-Rluc-GT3a-P89L by site-directed mutagenesis (Table 9). Two mutations, Q41R and A166T, were located at the NS3 protease domain, three mutations were located at A379T, S534G, and K583E at the NS3 helicase domain, and S1C was located at the NS4A protein. All of the additional mutations further augmented genotype 3a HCV RNA replication compared with P89L alone (FIG. 11A). For example, the P89L/A166T double mutation replicon achieved a peak replication level that was 19 times greater than the P89L single mutation replicon. Furthermore, when the P89L/A166T or P89L/K583E double mutation replicon was transfected into genotype 3a-permissive 3a-C3 cells, the replicon replication efficiency was further stimulated about 5-fold to a level that is comparable to the highly adapted genotype 1a or 1b replicons (FIG. 11B). Put together, a combination of selected host cells (e.g, 3a-C3 cells) and secondary adaptive mutation (e.g. A166T in NS3) established an efficient system to support genotype 3 HCV replication in cell culture that is comparable to those for genotype 1.

TABLE 9

Mutations analyzed in Rluc-neo-GT3a-P89L replicon cells lines

| No. of Clones | NS3 | NS4A |
|---|---|---|
| 3 | Q41R | — |
| 4 | A166T | — |
| 2 | A379T | — |
| 2 | S534G | — |
| 4 | K583E | — |
| 2 | — | S1C |

Evaluation of the Antiviral Activities of HCV Inhibitors Against Genotype 3a.

To investigate antiviral activity against genotype 3a, five different classes of HCV inhibitors were tested in a transient assay of the genotype 3a Pi-Rluc replicon: NS3 protease, NS5A, NS5B active site, NS5B non-active site, and host factor inhibitors. A standard genotype 1b Pi-Rluc replicon was tested in parallel. The transient replicon replication assays were performed in 1C cells to minimize the potential influence of host cell difference on compound antiviral activities. $EC_{50}$ values against both genotype 1b and genotype 3a replicons were successfully generated for all inhibitors using a high-throughput 384-well assay measuring Rluc activity (Table 10).

TABLE 10

Antiviral activities of HCV inhibitors against genotype 1b and 3a replicons

| Inhibitor Classes | Compounds | Pi-Rluc-GT3a-P89L/A166T EC50 (nM) | Pi-Rluc-GT3a-P89L/K583E EC50 (nM) | Pi-Rluc-GT1b EC50 (nM) | GT3a(P89L/A166T)/Ib EC50 Ratio | GT3a(P89L/K583E)/Ib EC50 Ratio |
|---|---|---|---|---|---|---|
| NS3 Protease | Telaprevir | 650 | 1330 | 407 | 1.6 | 3.27 |
| | Boceprevir | 460 | 273 | 188 | 2.44 | 1.45 |
| | GS-9451 | 1647 | 921 | 10 | 173 | 97 |
| | MK-5172 | 60 | 23 | 0.81 | 74 | 28 |
| | BILN-2061 | 447 | 95 | 0.93 | 478 | 102 |
| NS5A | GS-5885 | 92 | 40 | 0.0041 | 22370 | 9758 |
| | BMS-790052 | 0.31 | 0.45 | 0.03 | 11 | 15 |
| NS5B Nuc | GS-7977 | 12 | 5.8 | 40 | 0.31 | 0.15 |
| | 2-CMeA | 23 | 15 | 86 | 0.27 | 0.17 |
| NS5B Non-Nuc | GS-9669 | 230 | 125 | 3.8 | 61 | 33 |
| | MK-3281 | 277 | 180 | 587 | 0.47 | 0.31 |
| | GS-9190 | 42 | 46 | 3 | 17 | 18 |
| | Filibuvir | 2041 | 895 | 121 | 17 | 7.4 |
| | HCV-796 | 2.8 | 2.4 | 20 | 0.14 | 0.12 |
| Host Target | CsA | 111 | 62 | 81 | 1.37 | 0.76 |
| | SCY-635 | 78 | 59 | 65 | 1.2 | 0.91 |

Five different classes of HCV inhibitors as listed in the first column were evaluated for their antiviral activities against GT1b and GT3a Pi-Rluc replicon in a transient transfection high-throughput 384-well format by measuring renilla luciferase activity. Data presented in the table represent the mean of at least two independent experiments.

Inhibitors targeting host factors (CsA and SCY-635) had equivalent potency against both genotype 1b and 3a replicons. Inhibitors targeting the NS5B active site (2-CMeA or GS-7977) were 3- to 6-fold more active against genotype 3a compared with 1b. Antivirals that target non-active sites on NS5B polymerase, the NS5B thumb site I inhibitor MK-3281 and the palm site II NS5B inhibitor HCV-796, were about 2-fold and 7-fold, respectively, more active against genotype 3a compared with genotype 1b. In contrast, the NS5B thumb site II inhibitors filibuvir and GS-9669 and the palm site ½ inhibitor GS-9190 were approximately 17-, 60-, and 17-fold, respectively, less active against genotype 3a, versus genotype 1b. Although the NS5A inhibitor BMS-790052 was 11-fold less active against genotype 3a, it was still quite potent with $EC_{50}$ values of 0.31-0.45 nM against genotype 3a. Another NS5A inhibitor, GS-5885 (available from Gilead Sciences, Inc. Foster City, Calif.), was approximately 10.000-fold less active against genotype 3a compared with genotype 1b ($EC_{50}$ values for genotype 3a: 40-92 nM). The NS3 protease inhibitors boceprevir and telaprevir were slightly less potent (1.5- to 3.3-fold) against genotype 3a versus genotype 1b. However, the protease inhibitors BILN-2061, GS-9451, and MK-5127 were 28- to 478-fold less potent against genotype 3a versus genotype 1b. Overall, these results demonstrate that the transient transfection of a genotype 3a replicon system is robust and can serve as a valuable tool for drug discovery, lead compound optimization, and clinical virology applications.

It will be appreciated that those skilled in the art will be able to devise various arrangements which, although not explicitly described or shown herein, embody the principles of the disclosure and are included within its spirit and scope. Furthermore, all conditional language recited herein is principally intended to aid the reader in understanding the principles of the disclosure and the concepts contributed by the inventors to furthering the art, and are to be construed as being without limitation to such specifically recited conditions. Moreover, all statements herein reciting principles, aspects, and embodiments of the disclosure are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

The invention claimed is:

1. An isolated genotype 3a hepatitis C viral (HCV) RNA construct comprising a 5'NTR, an internal ribosome entry site (IRES), sequences encoding one or more of NS3, NS4A, NS4B, NS5A or NS5B, and a 3'NTR, wherein the RNA construct further comprises a mutation as compared to a wild-type HCV 3a sequence of SEQ ID NO:12, wherein said mutation is N607S or P89L, or both, in NS3, and wherein the mutation positions correspond to the residue positions in SEQ ID NO:13.

2. The RNA construct of claim 1, wherein the RNA construct comprise the mutation N607S in NS3.

3. The RNA construct of claim 1, wherein the RNA construct comprises the mutation P89L in NS3.

4. The RNA construct of claim 3, wherein the construct further comprises a mutation that is Q41R, A166T, A379T, S534G, or K583E in NS3, or S1C in NS4A.

5. The RNA construct of claim 1, wherein the construct further comprises a mutation S232I in NS5A.

6. The RNA construct of claim 1, further comprising a marker gene for selection.

7. The RNA construct of claim 6, wherein the marker gene is a neomycin phosphotransferase gene.

8. The RNA construct of claim 1, further comprising a reporter gene.

9. The RNA construct of claim 8, wherein the reporter gene is luciferase.

10. The RNA construct of claim 1, wherein the construct comprises, from 5' to 3', the 5'NTR, the IRES, sequences encoding NS3, NS4A, NS4B, NS5A and NS5B, and the 3'NTR.

11. The RNA construct of claim 1, further comprising a sequence encoding one or more of C, E1 or E2.

12. An isolated cell comprising a genotype 3a hepatitis C viral (HCV) RNA construct of claim 1.

13. The cell of claim 12, wherein there is an absence, in the cell, of a DNA construct encoding the RNA construct.

14. The cell of claim 12, wherein the cell comprises at least 10 copies of the RNA construct.

15. The cell of claim 12, wherein the RNA construct comprises a subgenomic HCV sequence.

16. The cell of claim 15, wherein the RNA construct comprises a 5'NTR, an internal ribosome entry site (IRES), sequences encoding NS3, NS4A, NS4B, NS5A and NS5B, and a 3'NTR.

17. The cell of claim 12, wherein the RNA construct comprises a full genome HCV sequence.

18. The cell of claim 12, where the RNA construct further comprises a mutation S232I in NS5A.

19. The cell of claim 12, wherein the RNA construct comprises the mutation N607S in NS3.

20. The cell of claim 12, wherein the RNA construct comprises the mutation P89L in NS3.

21. The cell of claim 12, wherein the cell is a mammalian cell.

22. The cell of claim 21, wherein the cell is a hepatoma cell.

23. The cell of claim 22, wherein the cell is a Huh7 1C cell.

24. The RNA construct of claim 1, wherein the RNA construct is capable of replication in the eukaryotic cell in vitro.

* * * * *

UNITED STATES PATENT AND TRADEMARK OFFICE

CERTIFICATE OF CORRECTION

PATENT NO. : 8,889,848 B2
APPLICATION NO. : 13/542551
DATED : November 18, 2014
INVENTOR(S) : William E. Delaney, IV et al.

It is certified that error appears in the above-identified patent and that said Letters Patent is hereby corrected as shown below:

IN THE CLAIMS:

In Column 57, Claim 2, Line 60, please replace "comprise" with --comprises--.

Signed and Sealed this
Tenth Day of March, 2015

Michelle K. Lee

Michelle K. Lee
*Deputy Director of the United States Patent and Trademark Office*